US008551943B2

(12) United States Patent
Bond et al.

(10) Patent No.: US 8,551,943 B2
(45) Date of Patent: *Oct. 8, 2013

(54) COMPOSITIONS AND METHODS FOR TREATING AIDS OR CANCER BY INHIBITING THE SECRETION OF MICROPARTICLES

(71) Applicants: Vincent Craig Bond, Stone Mountain, GA (US); Michael Powell, Douglasville, GA (US); Ming Bo Huang, Atlanta, GA (US); Syed Ali, Pinang (MY); Andrea D. Raymond, Atlanta, GA (US); Martin Neville Shelton, Stone Mountain, GA (US); Francois Jean Villinger, Decatur, GA (US)

(72) Inventors: Vincent Craig Bond, Stone Mountain, GA (US); Michael Powell, Douglasville, GA (US); Ming Bo Huang, Atlanta, GA (US); Syed Ali, Pinang (MY); Andrea D. Raymond, Atlanta, GA (US); Martin Neville Shelton, Stone Mountain, GA (US); Francois Jean Villinger, Decatur, GA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,597

(22) Filed: Sep. 17, 2012

(65) Prior Publication Data
US 2013/0018003 A1    Jan. 17, 2013

Related U.S. Application Data

(63) Continuation of application No. 12/783,829, filed on May 20, 2010.

(60) Provisional application No. 61/213,471, filed on Jun. 12, 2009.

(51) Int. Cl.
*A61P 31/12* (2006.01)
*A61P 31/18* (2006.01)
*A61K 39/00* (2006.01)
*A61K 39/21* (2006.01)
*C12N 5/22* (2006.01)

(52) U.S. Cl.
USPC ....... 514/3.7; 514/3.8; 424/184.1; 424/185.1; 424/188.1; 435/339.1

(58) Field of Classification Search
None
See application file for complete search history.

(56) References Cited

U.S. PATENT DOCUMENTS

| 6,551,795 B1 | 4/2003 | Rubenfield et al. |
| 7,476,386 B1 | 1/2009 | Gras-Masse et al. |
| 7,517,520 B2 | 4/2009 | Manolova et al. |
| 7,517,684 B2 | 4/2009 | Rubenfield et al. |
| 2003/0229906 A1 | 12/2003 | Gelman et al. |

FOREIGN PATENT DOCUMENTS

WO    99/03499    1/1999

OTHER PUBLICATIONS

Website: http://www.cellsignal.com/products/2368.html; to show "DYKDDDDK" as a kit; downloaded Jan. 12, 2013.*
Bergmann et al.; J. Immunology (1996); pp. 3242-3249.*
Nunn et al.; J. Virology, Sep. 1996; pp. 6157-6161.*
Website: http://www.cellsignal.com/products/2368.html; to show that "DYKDDDDK" as a kit; re-downloaded Feb. 8, 2013.*
Bergmann et al.; J. Immunology (1996); vol. 157, No. 8, pp. 3242-3249.*
Nunn et al.; J. Virology, Sep. 1996; 70(9), pp. 6157-6161.*
U.S. Patent Documents—none.*
Piguet et al.; Nat Cell Biol.; Mar. 2000; 2(3): 163-167 (made of record as Exhibit 1; Jun. 25, 2013.*
Pun, P. B. et al., "Intranasal administration of peptide antigens of HIV with mucosal adjuvant CpG ODN coentrapped in microparticles enhances the mucosal and systemic immune responses", International Immunopharmacology, vol. 9, (2009), pp. 468-477.
Zhang, H. et al., "Comparing Pooled Peptides with Intact Protein for Accessing Cross-presentation Pathways for Protective CD8+ and CD4+ T Cells*", The Journal of Biological Chemistry, vol. 284, No. 14, (2009), pp. 9184-9191.
European Search Report issued in European Patent Application No. 10786562.8, mailed Mar. 19, 2012.
Gahéry-Ségard et al., "Multiepitopic B- and T-cell responses induced in humans by a human immunodeficiency virus type 1 lipopeptide vaccine," Journal of Virology, 2000, pp. 1694-1703, vol. 74—Issue 4.
Pun et al., "Intranasal administration of peptide antigens of HIV with mucosal adjuvant CpG ODN coentrapped in microparticles enhances the mucosal and systemic immune responses," International Immunopharmacology, 2009, pp. 468-477, vol. 9—Issue 4.
Zhang et al., "Comparing pooled peptides with intact protein for accessing cross-presentation pathways for protective CD8+ and CD4+ T cells," Journal of Biological Chemistry, 2009, pp. 9184-9191, vol. 284—No. 14.
International Search Report and Written Opinion of the International Searching Authority issued in International Application No. PCT/US2010/035698 mailed Feb. 16, 2011.
Esser et al., "Differential Incorporation of CD45, CD80 (B7 -1), CD86 (B7 -2), and Major Histocompatibility 1 Complex Class I and II Molecules into Human Immunodeficiency Virus Type 1 Virions and Microvesicles: Implications for Viral Pathogenesis and Immune Regulation," Journal of Virology, Jul. 2001, pp. 6173-6182, vol. 75—No. 13.

(Continued)

*Primary Examiner* — Robert A Wax
*Assistant Examiner* — Jeffrey T Palenik
(74) *Attorney, Agent, or Firm* — Ping Wang; Andrews Kurth LLP

(57) ABSTRACT

Novel peptides that inhibit the release of microparticles from cells are disclosed. The peptide contains at least one VGFPV motif at the N-terminal and has a length of 10-100 amino acids. Also disclosed is polynucleotide encoding the peptide, expression vectors carrying the polynucleotide, and methods for treating AIDS and tumors using the novel peptides.

17 Claims, 22 Drawing Sheets

(56) References Cited

OTHER PUBLICATIONS

Grossman et al., "CD4+ T-cell depletion in HIV infection: Are we closer to understanding the cause?," Nature Medicine, Apr. 2002, pp. 319-323, vol. 8—No. 4.
Chen et al., "Activated STAT3 is a mediator and biomarker of VEGF endothelial activation," Cancer Biology & Therapy Dec. 2008, pp. 1994-2003, vol. 7—Issue 12.
Sanfridson et al., "Nef proteins encoded by human and simian immunodeficiency viruses induce the accumulation of endosomes and lysosomes in human T cells," Proceedings of the National Academy of Science, Feb. 1997, pp. 873-878, vol. 94.
Chalmin et al., "Membrane-associated Hsp72 from tumor-derived exosomes mediates STAT3-dependent 5 immunosuppressive function of mouse and human myeloid-derived suppressor cells," The Journal of Clinical Investigation, Feb. 2010, pp. 457-471, vol. 120—No. 2.
Campbell et al., "HIV-1 NEF Protein is Screted Into Vesicles That Can Fuse With Target Cells and Virons", Ethnicity & Disease, Spring 2008, pp. S2-13-S2-19, vol. 18—No. 2, Supplement 2.
Yu et al., "Tumor Exosomes Inhibit Differentiation of Bone Marrow Dendritic Cells," The Journal of Immunology, 2007, pp. 6867-6875, vol. 178.
Nickel, "Unconventional Secretory Routes: Direct Protein Export Across the Plasma Membrane of Mammalian Cells," Traffic, 2005, pp. 607-614, vol. 6.
Johnstone et al., "Vesicle Formation during Reticulocyte Maturation," The Journal of Biological Chemistry, Jul. 5, 1987, pp. 9412-9420, vol. 262—No. 19.
Lee et al., "Bi-Directional Protein Transport Between the ER and Golgi," Annual Review Cellular and Development Biology, 2004, pp. 87-123, vol. 20.
Yi et al., "Association of Mortalin (HSPA9) with Liver Cancer Metastasis and Prediction for Early Tumor 11 Recurrence," Molecular & Cellular Proteomics, 2008, pp. 315-325, vol. 7.2.
Walker et al., "Mortalin-Based Cytoplasmic Sequestration of p53 in a Nonmammalian Cancer Model," America Journal of Pathology, May 2006, pp. 1526-1530, vol. 168—No. 5.
Misumi et al., "Novel Blockade by Brefeldin a of Intracellular Transport of Secretory Proteins in Cultured Rat Hepatocytes," The Journal of Biological Chemistry, Aug. 25, 1986, pp. 11398-11403, vol. 261—No. 24.
All et al., "Genetic Characterization of HIV Type 1 Nef-Induced Vesicle Secretion," AIDS Research and Human Retroviruses, 2010, pp. 173-192, vol. 26—No. 2.
Parolini et al., "Microenvironmental pH Is a Key Factor for Exosome Traffic in Tumor Cells," The American Society for Biochemistry and Molecular Biology, Inc., pp. 1-19, dated Sep. 30, 2009.
Pilzer et al., "Mortalin Inhibitors Sensitize K562 leukemia cells to complement-dependent cytotOXicity," International Journal of Cancer, pp. 1-22, dated Sep. 8, 2009.
Deocaris et al., "Mortalln sensitizes human cancer cells to MKT-077-induced senescence," Cancer Letters, 2007, pp. 259-269, vol. 252.
Ciocca et al., "Heat shock proteins in cancer: diagnostic, prognostic, predictive, and treatment implications," Cell Stress & Chaperones, 2005, pp. 86-103, vol. 10—No. 2.
Calderwood, "Heat shock proteins in cancer: chaperones of tumorigenesis," TRENDS in Biochemical Sciences, 2006, pp. 164-172, vol. 31—No. 3.
Yu et al., "Tumor exosomes inhibit differentiation of bone marrow dendritic cells," Journal of Immunology, 2007, pp. 6867-6875, vol. 178—No. 11.
Pilzer et al.,"Emission of membrane vesicles: roles in complement resistance, immunity and cancer," Springer Seminars in Immunopathology, 2005, pp. 375-387, vol. 27—No. 3.
Czarnecka et al., "Mitochondrial chaperones in cancer: from molecular biology to clinical diagnostics," Cancer Biology & Therapy, 2006, pp. 714-720, vol. 5—No. 7.
Wadhwa et al., "Inactivation of tumor suppressor p53 by mot-2, a hsp70 family member," Journal of Biological Chemistry, 1998, pp. 29586-29591, vol. 273—No. 45.

Iero et al., "Tumour-released exosomes and their implications in cancer immunity," Cell Death and Differentiation, 2008, pp. 80-88, vol. 15—No. 1.
Savina et al., "Exosome release is regulated by a calcium-dependent mechanism in K562 cells", Journal of Biological Chemistry, 2003, pp. 20083-20090, vol. 278—No. 2.
Luo et al., "Kinetic and Structural Characterization of Human Mortalin," Protein Expression and Purification, 2010, pp. 1-7.
Wadhwa et al., "Can mortalin be a candidate target for cancer therapy?" Cancer Therapy, 2010, pp. 173-178, vol. 1.
Kaul et al., "Three faces of mortalin: a housekeeper, guardian and killer," Experimental Gerontology, 2007, pp. 263-274, vol. 42—No. 4.
Deocaris et al., "On tha brotherhood of the mitochondrial chaperones mortalin and heat shock protein 60," Cell Stress & Chaperones, 2006, pp. 116-128, vol. 11—No. 2.
Kanai at al., "Physical and functional interaction between mortalin and Mps1 kinase," Genes to Cells, 2007, pp. 797-810, vol. 12—No. 6.
Kaul et al., "Mortalin: present and prospective," Experimental Gerontology, 2002, pp. 1157-1164, vol. 37—No. 10-11.
Ma et al., "Mortalin controls centrosome duplication via modulating centrosomal localization of p53," Oncogene, 2006, pp. 5377-5390, vol. 25—No. 39.
Singh et al., "Cloning and some novel characteristics of mitochondrial Hsp70 from Chinese hamster cells," Experimental Cell Research, 1997, pp. 205-216, vol. 234—No. 2.
Vanbuskirk et al., "Cellular and subcellular distribution of PBP72/74, a peptide-binding protein that plays a role in antigen processing," Journal of Immunology, 1991, pp. 500-506, vol. 146—No. 2.
Kaul et al., "Activation of wild type p53 function by its mortalin-binding, cytoplasmically localizing carboxyl terminus peptides," Journal of Biological Chemistry, 2005, pp. 39373-39379, vol. 280—No. 47.
Mizukoshi et al., "Cell-cycle dependent tyrosine phosphorylation on mortalin regulates its interaction with fibroblast growth factor-1," Biochemical and Biophysical Research Communications, 2001, pp. 1203-1209, vol. 280—No. 4.
Mizukoshi et al., "Fibroblast growth factor-1 interacts with the glucose-regulated protein GRP75/mortalin," Biochemical Journal, 1999, pp. 461-466, vol. 343—No. 2.
Prudovsky et al., "Secretion without Golgi," Journal of Cellular Biochemistry, 2008, pp. 1327-1343, vol. 103—No. 5.
Pilzer et al., "Mortalin/GRP75 promotes release of membrane vesicles from immune attacked cells and protection from complement-mediated lysis," International Immunology, 2005, pp. 1239-1248, vol. 17—No. 9.
Choi et al., "Proteomic analysis of microvesicles derived from human colorectal cancer cells," Journal of Proteome Research, 2007, pp. 4646-4655, vol. 6—No. 12.
Staubach et al., "Proteomics of MUCl-contalning lipid rafts from plasma membranes and exosomes of human breast carcinoma cells MCF-7," Proteomics, 2009, pp. 2820-2835, vol. 9.
Wadhwa et al., "Upregulation of mortalin/mthsp70/Grp75 contributes to human carcinogenesis", International Journal of Cancer, 2006, pp. 2973-2980, vol. 118—No. 12.
Lippincott-Schwartz et al., "Rapid redistribution of Golgi proteins into the ER in cells treated with brefeldin A: evidence for membrane cycling from Golgi to ER," Cell, Mar. 10, 1989, pp. 801-813, vol. 56.
Muesch et al., "A novel pathway for secretory proteins?" Trends in Biochemical Sciences, Mar. 1990, pp. 86-88, vol. 15—No. 3.
Nickel, "Unconventional secretory routes: direct protein export across the plasma membrane of mammalian cells," Traffic, Aug. 2005, pp. 607-614, vol. 6—No. 8.
Guy et al., "Mutational analysis of the HIV nef protein," Virology, Jun. 1990, pp. 413-425, vol. 176—No. 2.
Calderwood et al., "Heat shock proteins: stress proteins with Janus-like properties in cancer," International Journal of Hyperthermia, Feb. 2008, pp. 31-39, vol. 24—No. 1.
Parolini et al., "Microenvironmental pH is a key factor for exosome traffic in tumor cells," Journal of Biological Chemistry, Dec. 4, 2009, pp. 34211-22, vol. 284—No. 49.

* cited by examiner

Synthetic peptides

Vector constructs

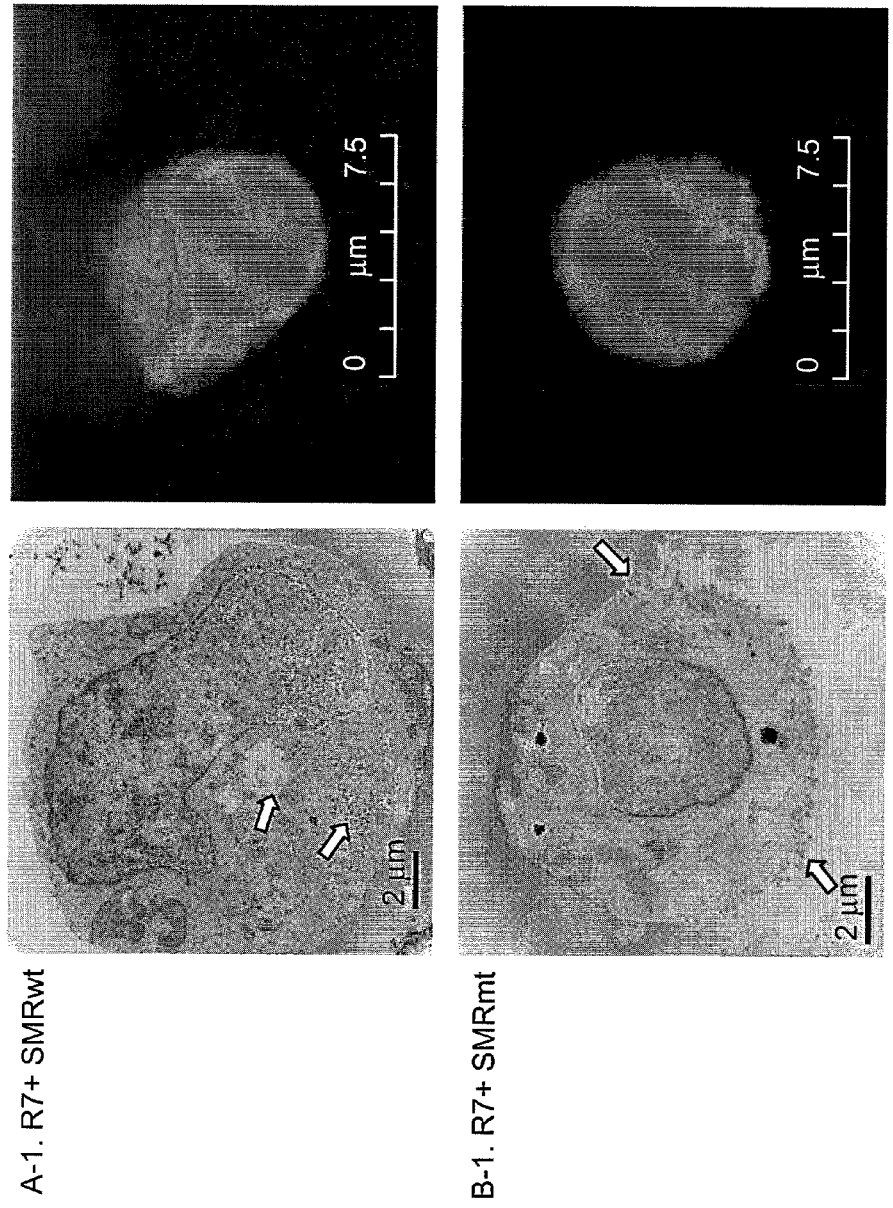

SEQUENCE LISTING

```
<160> NUMBER OF SEQ ID NOS: 7

<210> SEQ ID NO 1
<211> LENGTH: 5
<212> TYPE: PRT
<213> ORGANISM: artificial
<220> FEATURE:
<223> OTHER INFORMATION: synthetic peptide

<400> SEQUENCE: 1

Val Gly Phe Pro Val
1               5

<210> SEQ ID NO 2
<211> LENGTH: 12
<212> TYPE: PRT
<213> ORGANISM: artificial
<220> FEATURE:
```

```
<223> OTHER INFORMATION: synthetic peptide

<400> SEQUENCE: 2

Val Gly Phe Pro Val Ala Ala Val Gly Phe Pro Val
1               5                   10

<210> SEQ ID NO 3
<211> LENGTH: 20
<212> TYPE: PRT
<213> ORGANISM: Artificial Sequence
<220> FEATURE:
<223> OTHER INFORMATION: synthetic peptide

<400> SEQUENCE: 3

Val Gly Phe Pro Val Ala Ala Val Gly Phe Pro Val Asp Tyr Lys Asp
1               5                   10                  15

Asp Asp Asp Lys
            20

<210> SEQ ID NO 4
<211> LENGTH: 20
<212> TYPE: PRT
<213> ORGANISM: Artificial Sequence
<220> FEATURE:
<223> OTHER INFORMATION: synthetic peptide

<400> SEQUENCE: 4

Ala Gly Phe Pro Val Ala Ala Ala Gly Phe Pro Val Asp Tyr Lys Asp
1               5                   10                  15

Asp Asp Asp Lys
            20

<210> SEQ ID NO 5
<211> LENGTH: 6840
<212> TYPE: DNA
<213> ORGANISM: Artificial Sequence
<220> FEATURE:
<223> OTHER INFORMATION: plasmid

<400> SEQUENCE: 5
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcc tcgaggcctg gccattgcat acgttgtatc     240
catatcataa tatgacattt atattggctc atgtccaaca ttaccgccat gttgacattg     300
attattgact agttattaat agtaatcaat tacggggtca ttagttcata gcccatatat     360
ggagttccgc gttacataac tacggtaaat ggcccgcctg gctgaccgcc caacgacccc     420
cgcccattga cgtcaataat gacgtatgtt cccatagtaa cgccaatagg gactttccat     480
tgacgtcaat gggtggagta tttacggtaa actgcccact ggcagtaca tcaagtgtat     540 catatgccaa gtacgccccc tattgacgtc aatgacggta aatggcccgc ctggcattat     600
gcccagtaca tgaccttatg gactttcct acttggcagt acatctacgt attagtcatc     660
gctattacca tggtgatgcg gttttggcag tacatcaatg ggcgtggata gcggtttgac     720
tcacggggat ttccaagtct ccaccccatt gacgtcaatg ggagttgttt ggcaccaaa     780 atcaacggga ctttccaaaa tgtcgtaaca actccgcccc attgacgcaa atgggcggta     840
ggcgtgtacg gtgggaggtc tatataagca gagctcgttt agtgaaccgt cagatcgcct     900
ggagacgcca tccacgctgt tttgacctcc atagaagaca ccgggaccga tccagcctcc     960
```

```
gcgggcgcgc atgggtggca agtggtcaaa aagtagtgtg attggatggc ctgctgtaag    1020
ggaaagaatg agacgagctg agccagcagc agatggggtg ggagcagtat ctcgagacct    1080
agaaaaacat ggagcaatca caagtagcaa tacagcagct aacaatgctg cttgtgcctg    1140
gctagaagca caagaggagg aagaggtggg ttttccagtc acacctcagg tacctttaag    1200
accaatgact tacaaggcag ctgtagatct tagccacttt ttaaaagaaa aggggggact    1260
ggaagggcta attcactccc aaagaagaca agatatcctt gatctgtgga tctaccacac    1320
acaaggctac ttccctgatt ggcagaacta cacaccaggg ccaggggtca gatatccact    1380
gacctttgga tggtgctaca agctagtacc agttgagcca gataaggtag aagaggccaa    1440
taaaggagag aacaccagct tgttacaccc tgtgagcctg catggaatgg atgaccctga    1500
gagagaagtg ttagagtgga ggtttgacag ccgcctagca tttcatcacg tggcccgaga    1560
gctgcatccg gagtacttca agaactgcgg tgcaggagct agcaaaggag aagaactctt    1620
cactggagtt gtcccaattc ttgttgaatt agatggtgat gttaacggcc acaagttctc    1680
tgtcagtgga gagggtgaag gtgatgcaac atacggaaaa cttaccctga agttcatctc    1740
actactggca aactgcctgt ccatggcca acactagtca ctactctgtg ctatggtgtt    1800
caatgctttt caagataccc ggatcatatg aaacggcatg acttttcaa gagtgccatg    1860
cccgaagtta tgtacaggaa aggaccatct tcttcaaaga tgacggcaac tacaagacac    1920
gtgctgaagt caagtttgaa ggtgataccc ttgttaatag aatcgagtta aaaggtattg    1980
acttcaagga agatggcaac attctgggac acaaattgga atacaactat aactcacaca    2040
atgtatacat catggcagac aaacaaaaga tggaatcaa agtgaacttc aagacccgcc    2100
acaacattga gatggaagc gttcaactag cagaccatta tcaacaaaat actccaattg    2160
gcgatggccc tgtccttta ccagacaacc attacctgtc cacacaatct gccctttcga    2220
aagatcccaa cgaaaagaga gaccacatgg tccttcttga gtttgtaaca gctgctggga    2280
ttacacatgg catggatgaa ctgtacaact gaggatccac tagtaacggc cgccagtgtg    2340
ctggaattct gcagatatcc atcacactgg cggccgctcg agcatgcatc tagagggccc    2400
tattctatag tgtcacctaa atgctagagc tcgctgatca gcctcgactg tgccttctag    2460
ttgccagcca tctgttgttt gcccctcccc gtgccttcct tgaccctgga aggtgccact    2520
cccactgtcc tttcctaata aaatgaggaa attgcatcgc attgtctgag taggtgtcat    2580
tctattctgg ggggtggggt ggggcaggac agcaagggg aggattggga agacaatagc    2640
aggcatgctg gggatgcggt gggctctatg gcttctgagg cggaaagaac cagctggggc    2700
tctaggggt atccccacgc gccctgtagc ggcgcattaa gcgcggcggg tgtggtggtt    2760
acgcgcagcg tgaccgctac acttgccagc gccctagcgc ccgctccttt cgctttcttc    2820
ccttcctttc tcgccacgtt cgccggcttt ccccgtcaag tctaaatcgg ggcatccctt    2880
tagggttccg atttagtgct ttacggcacc tcgaccccaa aaaacttgat tagggtgatg    2940
gttcacgtag tgggccatcg cccigataga cggtttttcg ccctttgagt tggagtccac    3000
gttctttaat agtggactct tgttccaaac tggaacaaca ctcaaccta tctcggtcta    3060
ttcttttgat ttataaggga ttttgggat ttcggcctat tggttaaaaa atgagcgatt    3120
taacaaaaat ttaacgcgaa ttaattctgt ggaatgtgtg tcagttaggg tgtggaaagt    3180
ccccaggctc cccaggcagg cagaagtatg caaagcatgc atctcaatta gtcagcaacc    3240
aggtgtggaa agtccccagg ctccccagca ggcagaagta tgcaaagcat gcatctcaat    3300
tagtcagcaa ccatagtccc gcccctaact ccgcccatcc cgcccctaac tccgcccagt    3360
```

```
tccgcccatt ctccgcccca tggctgacta attttttta tttatgcaga ggccgaggcc    3420
gcctctgcct ctgagctatt ccagaagtag tgaggaggct ttttggagg cctaggcttt    3480 tgcaaaaagc tcccggagct tgtatatcca ttttcggatc tgatcaagag acaggatgag    3540
gatcgtttcg catgattgaa caagatggat tgcacgcagg ttctccggcc gcttgggtgg    3600
agaggctatt cggctatgac tgggcacaac agacaatcgg ctgctctgat gccgccgtgt    3660
tccggctgtc agcgcagggg cgcccggttc tttttgtcaa gaccgacctg tccggtgccc    3720
tgaatgaact gcaggacgag gcagcgcggc tatcgtggct ggccacgacg ggcgttcctt    3780
gcgcagctgt gctcgacgtt gtcactgaag cgggaaggga ctggctgcta ttgggcgaag    3840
tgccggggca ggatctcctg tcatctcacc ttgctcctgc cgagaaagta tccatcatgg    3900
ctgatgcaat gcggcggctg catacgcttg atccggctac ctgcccattc gaccaccaag    3960
cgaaacatcg catcgagcga gcacgtactc ggatggaagc cggtcttgtc gatcaggatg    4020
atctggacga agagcatcag gggctcgcgc cagccgaact gttcgccagg ctcaaggcgc    4080
gcatgcccga cggcgaggat ctcgtcgtga cccatggcga tgcctgcttg ccgaatatca    4140
tggtggaaaa tggccgcttt tctggattca tcgactgtgg ccggctgggt gtggcggacc    4200
gctatcagga catagcgttg gctacccgtg atattgctga agagcttggc ggcgaatggg    4260
ctgaccgctt cctcgtgctt tacggtatcg ccgctcccga ttcgcagcgc atcgccttct    4320
atcgccttct tgacgagttc ttctgagcgg gactctgggg ttcgaaatga ccgaccaagc    4380
gacgcccaac ctgccatcac gagatttcga ttccaccgcc gccttctatg aaaggttggg    4440
cttcggaatc gttttccggg acgccggctg atgatcctc cagcgcgggg atctcatgct    4500
ggagttcttc gcccacccca acttgtttat tgcagcttat aatggttaca ataaagcaa    4560 tagcatcaca aatttcacaa ataaagcatt ttttcactg cattctagtt gtggttgtcc    4620
aaactcatca atgtatctta tcatgtctgt ataccgtcga cctctagcta gagcttggcg    4680
taatcatggt catagctgtt tcctgtgtga aattgttatc cgctcacaat tccacacaac    4740
atacgagcgg aagcataaag tgtaaagcct ggggtgccta atgagtgagc taactcacat    4800
taattgcgtt gcgctcactg cccgctttcc agtcgggaaa cctgtcgtgc cagctgcatt    4860
aatgaatcgg ccaacgcgcg gggagaggcg gtttgcgtat tgggcgctct tccgcttcct    4920
cgctcactga ctcgctgcgc tcggtcgttc ggctgcggcg agcggtatca gctcactcaa    4980
aggcggtaat acggttatcc acagaatcag gggataacgc aggaaagaac atgtgagcaa    5040
aaggccagca aaaggccagg aaccgtaaaa aggccgcgtt gctggcgttt ttccataggc    5100 tccgccccc tgacgagcat cacaaaaatc gacgctcaag tcagaggtgg cgaaacccga    5160
caggactata aagataccag gcgtttcccc ctggaagctc cctcgtgcgc tctcctgttc    5220
cgaccctgcc gcttaccgga tacctgtccg cctttctccc ttcgggaagc gtggcgcttt    5280
ctcaatgctc acgctgtagg tatctcagtt cggtgtaggt cgttcgctcc aagctgggct    5340
gtgtgcacga accccccgtt cagcccaccg ctgcgcctta tccggtaact atcgtcttga    5400
gtccaacccg gtaagacacg acttatcgcc actggcagca gccactggta acaggattag    5460
cagagcgagg tatgtaggcg gtgctacaga gttcttgaag tggtggccta actacggcta    5520
cactagaagg acagtatttg gtatctgcgc tctgctgaag ccagttacct tcggaaaaag    5580
agttggtagc tcttgatccg gcaaacaaac caccgctggt agcggtggtt ttttgtttg    5640 caagcagcag attacgcgca gaaaaaagg atctcaagaa gatcctttga tcttttctac    5700
ggggtctgac gctcagtgga acgaaaactc acgttaaggg attttggtca tgagattatc    5760
```

```
aaaaaggatc ttcacctaga tccttttaaa ttaaaaatga agttttaaat caatctaaag    5820
tatatatgag taaacttggt ctgacagtta ccaatgctta atcagtgggc acctatctca    5880
gcgatctgtc tatttcgttc atccatagtt gcctgactcc ccgtcgtgta gataactacg    5940
atacgggagg gcttaccatc tggccccagt gctgcaatga taccgcgaga cccacgctca    6000
ccggctccag atttatcagc aataaaccag ccagccggaa gggccgagcg cagaagtggt    6060
cctgcaactt tatccgcctc catccagtct attaattgtt gccgggaagc tagagtaagt    6120
agttcgccag ttaatagttt gcgcaacgtt gttgccattg ctacaggcat cgtggtgtca    6180
cgctcgtcgt ttggtatggc ttcattcagc tccggttccc aacgatcaag gcgagttaca    6240
tgatccccat gttgtgcaaa aaagcggtta gctccttcgg tcctccgatc gttgtcagaa    6300
gtaagttggc cgcagtgtta tcactcatgg ttatggcagc actgcataat tctcttactg    6360
tcatgccatc cgtaagagct tttctgtgac tggtgagtac tcaaccaagt cattctgaga    6420
atagtgtatg cggcgaccga gttgctcttg cccggcgtca atacgggata ataccgcgcc    6480
acatagcaga actttaaaag tgctcatcat tggaaaacgt tcttcggggc gaaaactctc    6540
aaggatctta ccgctgttga gatccagttc gatgtaaccc actcgtgcac ccaactgatc    6600
ttcagcatct tttactttca ccagcgtttc tgggtgagca aaacaggaag gcaaaatgcc    6660
gcaaaaaagg gaataagggc gacacggaaa tgttgaatac tcatactctt cctttttcaa    6720
tattattgaa gcatttatca gggttattgt ctcatgagcg gatacatatt tgaatgtatt    6780
tagaaaaata aacaaatagg ggttccgcgc acatttcccc gaaaagtgcc acctgacgtc    6840
```

<210> SEQ ID NO 6
<211> LENGTH: 6857
<212> TYPE: DNA
<213> ORGANISM: Artificial Sequence
<220> FEATURE:
<223> OTHER INFORMATION: plasmid

<400> SEQUENCE: 6

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcc tcgaggcctg gccattgcat acgttgtatc     240
catatcataa tatgtacatt tatattggct catgtccaac attaccgcca tgttgacatt     300
gattattgac tagttattaa tagtaatcaa ttacggggtc attagttcat agcccatata     360
tggagttccg cgttacataa cttacggtaa atggcccgcc tggctgaccg cccaacgacc     420
cccgcccatt gacgtcaata atgacgtatg ttcccatagt aacgccaata gggactttcc     480
attgacgtca atgggtggag tatttacggt aaactgccca cttggcagta catcaagtgt     540
atcatatgcc aagtacgccc cctattgacg tcaatgacgg taaatggccc gcctggcatt     600
atgcccagta catgacctta tgggactttc ctacttggca gtacatctac gtattagtca     660
tcgctattac catggtgatg cggttttggc agtacatcaa tgggcgtgga tagcggtttg     720
actcacgggg atttccaagt ctccacccca ttgacgtcaa tgggagtttg ttttggcacc     780
aaaatcaacg ggactttcca aaatgtcgta acaactccgc cccattgacg caaatgggcg     840
gtaggcgtgt acggtgggag gtctatataa gcagagctcg tttagtgaac cgtcagatcg     900
cctggagacg ccatccacgc tgttttgacc tccatagaag acaccgggac cgatccagcc     960
tccgcgggcg cgcatgggtg gcaagtggtc aaaaagtagt gtgattggat ggcctgctgt    1020
```

```
aagggaaaga atgagacgag ctgagccagc agcagatggg gtgggagcag tatctcgaga    1080
cctagaaaaa catggagcaa tcacaagtag caatacagca gctaacaatg ctgcttgtgc    1140
ctggctagaa gcacaagagg aggaagaggc ggctgctgca gccacacctc aggtaccttt    1200
aagaccaatg acttacaagg cagctgtaga tcttagccac ttttttaaaag aaaagggggg    1260
actggaaggg ctaattcact cccaaagaag acaagatatc cttgatctgt ggatctacca    1320
cacacaaggc tacttccctg attggcagaa ctacacacca gggccagggg tcagatatcc    1380
actgaccttt ggatggtgct acaagctagt accagttgag ccagataagg tagaagaggc    1440
caataaagga gagaacacca gcttgttaca ccctgtgagc ctgcatggaa tggatgaccc    1500
tgagagagaa gtgttagagt ggaggtttga cagccgccta gcatttcatc acgtggcccg    1560
agagctgcat ccggagtact tcaagaactg cggtgcagga gctagcaaag gagaagaact    1620
cttcactgga gttgtcccaa ttcttgttga attagatggt gatgttaacg gccacaagtt    1680
ctctgtcagt ggagagggtg aaggtgatgc aacatacgga aaacttaccc tgaagttcat    1740
ctgcactact ggcaaactgc ctgttccatg gccaacacta gtcactactc tgtgctatgg    1800
tgttcaatgc ttttcaagat acccggatca tatgaaacgg catgactttt tcaagagtgc    1860
catgcccgaa ggttatgtac aggaaaggac catcttcttc aaagatgacg caactacaa     1920
gacacgtgct gaagtcaagt ttgaaggtga taccctcgtt aatagaatcg agttaaaagg    1980
tattgacttc aaggaagatg gcaacattct gggacacaaa ttggaataca actataactc    2040
acacaatgta tacatcatgg cagacaaaca aaagaatgga atcaaagtga acttcaagac    2100
ccgccacaac attgaagatg gaagcgttca actagcagac cattatcaac aaaatactcc    2160
aattggcgat ggccctgtcc ttttaccaga caaccattac ctgtccacac aatctgccct    2220
ttcgaaagat cccaacgaaa agagagacca catggtcctt cttgagtttg taacagctgc    2280
tgggattaca catggcatgg atgaactgta caactgagga tccactagta acggccgcca    2340
gtgtgctgga attctgcaga tatccatcac actggcggcc gctcgagcat gcatctagag    2400
ggccctattc tatagtgtca cctaaatgct agagctcgct gatcagcctc gactgtgcct    2460
tctagttgcc agccatctgt tgtttgcccc tcccccgtgc cttccttgac cctggaaggt    2520
gccactccca ctgtcctttc ctaataaaat gaggaaattg catcgcattg tctgagtagg    2580
tgtcattcta ttctgggggg tggggtgggg caggacagca agggggagga ttgggaagac    2640
aatagcaggc atgctgggga tgcggtgggc tctatggctt ctgaggcgga agaaccagc     2700
tggggctcta gggggtatcc ccacgcgccc tgtagcggcg cattaagcgc ggcgggtgtg    2760
gtggttacgc gcagcgtgac cgctacactt gccagcgccc tagcgcccgc tcctttcgct    2820
ttcttccctt cctttctcgc cacgttcgcc ggctttcccc gtcaagctct aaatcggggc    2880
atccctttag ggttccgatt tagtgcttta cggcacctcg accccaaaaa acttgattag    2940
ggtgatggtt cacgtagtgg gccatcgccc tgatagacgg ttttcgccc  tttgacgttg    3000
gagtccacgt tctttaatag tggactcttg ttccaaactg gaacaacact caaccctatc    3060
tcggtctatt cttttgattt ataagggatt ttggggattt cggcctattg gttaaaaaat    3120
gagctgattt aacaaaaatt taacgcgaat taattctgtg gaatgtgtgt cagttagggt    3180
gtggaaagtc cccaggctcc ccaggcaggc agaagtatgc aaagcatgca tctcaattag    3240
tcagcaacca ggtgtggaaa gtccccaggc tccccagcag gcagaagtat gcaaagcatg    3300
catctcaatt agtcagcaac catagtcccg cccctaactc cgcccatccc gcccctaact    3360
ccgcccagtt ccgcccattc tccgccccat ggctgactaa ttttttttat ttatgcagag    3420
```

```
gccgaggccg cctctgcctc tgagctattc cagaagtagt gaggaggctt ttttggaggc    3480
ctaggctttt gcaaaaagct cccgggagct tgtatatcca ttttcggatc tgatcaagag    3540
acaggatgag gatcgtttcg catgattgaa caagatggat tgcacgcagg ttctccggcc    3600
gcttgggtgg agaggctatt cggctatgac tgggcacaac agacaatcgg ctgctctgat    3660
gccgccgtgt tccggctgtc agcgcagggg cgcccggttc ttttttgtcaa gaccgacctg    3720 tccggtgccc tgaatgaact gcaggacgag gcagcgcggc tatcgtggct ggccacgacg    3780
ggcgttcctt gcgcagctgt gctcgacgtt gtcactgaag cgggaaggga ctggctgcta    3840
ttgggcgaag tgccggggca ggatctcctg tcatctcacc ttgctcctgc cgagaaagta    3900
tccatcatgg ctgatgcaat gcggcggctg catacgcttg atccggctac ctgcccattc    3960
gaccaccaag cgaaacatcg catcgagcga gcacgtactc ggatggaagc cggtcttgtc    4020
gatcaggatg atctggacga agagcatcag gggctcgcgc cagccgaact gttcgccagg    4080
ctcaaggcgc gcatgcccga cggcgaggat ctcgtcgtga cccatggcga tgcctgcttg    4140
ccgaatatca tggtggaaaa tggccgcttt tctggattca tcgactgtgg ccggctgggt    4200
gtggcggacc gctatcagga catagcgttg gctacccgtg atattgctga agagcttggc    4260
ggcgaatggg ctgaccgctt cctcgtgctt tacggtatcg ccgctcccga ttcgcagcgc    4320
atcgccttct atcgccttct tgacgagttc ttctgagcgg gactctgggg ttcgaaatga    4380
ccgaccaagc gacgcccaac ctgccatcac gagatttcga ttccaccgcc gccttctatg    4440
aaaggttggg cttcggaatc gttttccggg acgccggctg gatgatcctc cagcgcgggg    4500
atctcatgct ggagttcttc gcccacccca acttgtttat tgcagcttat aatggttaca    4560
aataaagcaa tagcatcaca aatttcacaa ataaagcatt tttttcactg cattctagtt    4620
gtggtttgtc caaactcatc aatgtatctt atcatgtctg tataccgtcg acctctagct    4680
agagcttggc gtaatcatgg tcatagctgt ttcctgtgtg aaattgttat ccgctcacaa    4740
ttccacacaa catacgagcc ggaagcataa agtgtaaagc ctggggtgcc taatgagtga    4800
gctaactcac attaattgcg ttgcgctcac tgcccgcttt ccagtcggga aacctgtcgt    4860
gccagctgca ttaatgaatc ggccaacgcg cggggagagg cggtttgcgt attgggcgct    4920
cttccgcttc ctcgctcact gactcgctgc gctcggtcgt tcggctgcgg cgagcggtat    4980
cagctcactc aaaggcggta atacggttat ccacagaatc aggggataac gcaggaaaga    5040
acatgtgagc aaaaggccag caaaaggcca ggaaccgtaa aaaggccgcg ttgctggcgt    5100
ttttccatag gctccgcccc cctgacgagc atcacaaaaa tcgacgctca agtcagaggt    5160
ggcgaaaccc gacaggacta taaagatacc aggcgtttcc ccctggaagc tccctcgtgc    5220
gctctcctgt tccgaccctg ccgcttaccg gatacctgtc cgcctttctc ccttcgggaa    5280
gcgtggcgct ttctcaatgc tcacgctgta ggtatctcag ttcggtgtag tcgttcgct    5340 ccaagctggg ctgtgtgcac gaaccccccg ttcagcccga ccgctgcgcc ttatccggta    5400
actatcgtct tgagtccaac ccggtaagac acgacttatc gccactggca gcagccactg    5460
gtaacaggat tagcagagcg aggtatgtag gcggtgctac agagttcttg aagtggtggc    5520
ctaactacgg ctacactaga aggacagtat ttggtatctg cgctctgctg aagccagtta    5580
ccttcggaaa aagagttggt agctcttgat ccggcaaaca aaccaccgct ggtagcggtg    5640
gtttttttgt ttgcaagcag cagattacgc gcagaaaaaa aggatctcaa gaagatcctt    5700
tgatcttttc tacggggtct gacgctcagt ggaacgaaaa ctcacgttaa gggattttgg    5760
tcatgagatt atcaaaaagg atcttcacct agatcctttt aaattaaaaa tgaagtttta    5820
```

```
-continued aatcaatcta aagtatatat gagtaaactt ggtctgacag ttaccaatgc ttaatcagtg   5880
aggcacctat ctcagcgatc tgtctatttc gttcatccat agttgcctga ctccccgtcg   5940
tgtagataac tacgatacgg gagggcttac catctggccc cagtgctgca atgataccgc   6000
gagacccacg ctcaccggct ccagatttat cagcaataaa ccagccagcc ggaagggccg   6060
agcgcagaag tggtcctgca actttatccg cctccatcca gtctattaat tgttgccggg   6120
aagctagagt aagtagttcg ccagttaata gtttgcgcaa cgttgttgcc attgctacag   6180
gcatcgtggt gtcacgctcg tcgtttggta tggcttcatt cagctccggt tcccaacgat   6240
caaggcgagt tacatgatcc cccatgttgt gcaaaaaagc ggttagctcc ttcggtcctc   6300
cgatcgttgt cagaagtaag ttggccgcag tgttatcact catggttatg gcagcactgc   6360
ataattctct tactgtcatg ccatccgtaa gatgcttttc tgtgactggt gagtactcaa   6420
ccaagtcatt ctgagaatag tgtatgcggc gaccgagttg ctcttgcccg gcgtcaatac   6480
gggataatac cgcgccacat agcagaactt taaaagtgct catcattgga aaacgttctt   6540
cggggcgaaa actctcaagg atcttaccgc tgttgagatc cagttcgatg taacccactc   6600
gtgcacccaa ctgatcttca gcatctttta ctttcaccag cgtttctggg tgagcaaaaa   6660
caggaaggca aaatgccgca aaaaagggaa taagggcgac acggaaatgt tgaatactca   6720
tactcttcct ttttcaatat tattgaagca tttatcaggg ttattgtctc atgagcggat   6780
acatatttga atgtatttag aaaaataaac aaatagggt tccgcgcaca tttccccgaa    6840
aagtgccacc tgacgtc                                                  6857

<210> SEQ ID NO 7
<211> LENGTH: 11
<212> TYPE: PRT
<213> ORGANISM: Artificial Sequence
<220> FEATURE:
<223> OTHER INFORMATION: peptide

<400> SEQUENCE: 7

Ala Leu Ala Glu Thr Cys Gln Asn Ala Trp Ala
1               5                   10
```

COMPOSITIONS AND METHODS FOR TREATING AIDS OR CANCER BY INHIBITING THE SECRETION OF MICROPARTICLES

RELATED APPLICATIONS

This application is a continuation of U.S. patent application Ser. No. 12/783,829, filed May 20, 2010, which claims priority from Provisional Patent Application 61/213,471 filed Jun. 12, 2009. The entirety of the aforementioned applications is incorporated herein by reference.

FIELD

The present invention generally relates to medical treatment and, in particular, to a method for treating AIDS or tumors by inhibiting the secretion of microparticles.

BACKGROUND

Membrane vesicles are spherical membrane microparticles, generally less than 200 nm in diameter. The microparticles are composed of a lipid bilayer containing a cytosolic fraction. Particular membrane vesicles are more specifically produced by cells, from intracellular compartments through fusion with the cytoplasmic membrane of a cell, resulting in their release into the extracellular biological fluids of an organism or into the supernatant of cells in culture. These vesicles/microparticles may be released in a number of ways. The classical secretory pathway processes mainly traditional membrane signals bearing receptors through the Endoplasmic Reticulum (ER) membrane (Lee et al., (2004) Annu. Rev. Cell Dev. Biol. 20, 87-123).

The secretory proteins are packaged into transport vesicles, delivered to the Golgi apparatus, and eventually released of into the extracellular space.

Alternatively, nonclassical secretory pathways exist and mediate translocation of cytosolic, nonsignal bearing molecules into the extracellular space (Lippincott-Schwartz et al., (1989) Cell 56, 801-813; and Misumi et al., (1986) J. Biol. Chem. 261, 11398-11403). Two of these involve intracellular vesicles of the endocytic membrane system, such as secretory lysosomes (Muesch et al., (1990) Trends Biochem. Sci. 15, 86-88) and exosomes (Johnstone et al., (1987) J. Biol. Chem. 262, 9412-9420), the latter ones being internal vesicles of late endosomes or multivesicular bodies (MVB). Lysosomal contents gain access to the exterior of cells when specialized endocytic structures such as secretory lysosomes of cytotoxic T lymphocytes fuse with the plasma membrane. Lumenal contents of late endocytic structures are released into the extracellular space when MVBs fuse with the plasma membrane resulting in release of the internal multivesicular endosomes into the extracellular space (called exosomes) along with their cargo molecules. Other nonclassical pathways involve direct translocation of cytosolic factors across the plasma membrane using protein conducting channels or a process called membrane blebbing (Nickel, W. (2005) Traffic. 6, 607-614). Membrane blebbing is characterized by shedding of plasma membrane-derived microvesicles into the extracellular space.

Microparticle release has been demonstrated from different cell types in varied physiological contexts. It has been demonstrated that tumor cells secrete microparticles, such as exosomes; texosomes, Tex or tumor exosomes (Yu et al., (2007) J. Immunol. 178, 6867-6875) in a regulated manner, carrying tumor antigens and capable of presenting these antigens or transmitting them to antigen presenting cells (patent application No. WO99/03499). These microparticles are released by tumor cells and cause immune suppression through immune cell killing or deregulation allowing tumor growth. Release of these FasL or TNF containing exosomes has been found to be one mechanism by which the tumor promotes a state of immune privilege/immune suppression. Alternatively, it has shown that HIV infected cells release Nef-containing vesicles (Guy et al., (1990) Virology 176, 413-425; and Campbell et al., (2008) Ethn. Dis. 18, S2-S9). We postulate that these vesicles are similarly used by HIV to dysregulate the immune system allowing HIV to survive. Finally, the endosomal trafficking pathway has been suggested to also be involved in virion release from infected cells (Sanfridson et al., (1997) Proc. Natl. Acad. Sci. U.S.A 94, 873-878; and Esser et al., (2001) J Virol. 75, 6173-6182). Thus, during the HIV infection, the endosomal pathway, involved in several vesicle release pathways, serves a dual function in both regulation of the immune system and in virion release of infected cells. It would be of particular interest to have an effective method that could be used to dampen or inhibit microparticle/vesicle release.

SUMMARY

One aspect of the present invention relates to a novel peptide that inhibits the release of microparticles from cells. The peptide has a length of 10-100 amino acids and contains (1) at least one VGFPV (SEQ ID NO: 1) motif at the N-terminal, or (2) at least one VGFPV (SEQ ID NO: 1) motif at the C-terminal, or (3) at least two VGFPV (SEQ ID NO: 1) motifs.

In one embodiment, the peptide contains at least one VGFPV (SEQ ID NO: 1) motif at the N-terminal. In another embodiment, the peptide contains at least one VGFPV (SEQ ID NO: 1) motif at the C-terminal. In another embodiment, the peptide contains at least two VGFPV (SEQ ID NO: 1) motifs. In another embodiment, the peptide contains the amino acid sequence VGFPVAAVGFPV (SEQ ID NO: 2). In yet another embodiment, the peptide has the sequence of H2N-VGFPVAAVGFPVDYKDDDDK-OH (SEQ ID NO: 3).

Another aspect of the present invention relates to a polynucleotide encoding the novel peptide of the present invention and an expression vector carrying a polynucleotide encoding the novel peptide of the present invention.

Another aspect of the present invention relates to a pharmaceutical composition for treating AIDS or tumors. The pharmaceutical composition comprises (1) a peptide has a length of 10-100 amino acids and contains (a) at least one VGFPV (SEQ ID NO: 1) motif at the N-terminal, or (b) at least one VGFPV (SEQ ID NO: 1) motif at the C-terminal, or (c) at least two VGFPV (SEQ ID NO: 1) motifs or an expression vector encoding such a peptide, and (2) a pharmaceutically acceptable carrier.

Another aspect of the present invention relates to a method for treating AIDS. The method comprises administering to a subject in need of such treatment an effective amount of a peptide containing at least one SEQ ID NO: 1 motif and having a length of 10-100 amino acids.

Another aspect of the present invention relates to a method for treating tumors. The method comprises administering to a subject in need of such treatment an effective amount of a peptide containing at least one SEQ ID NO: 1 motif and having a length of 10-100 amino acids.

BRIEF DESCRIPTION OF THE DRAWINGS

FIG. 4C is a composite of confocal and electron microscope pictures showing viral particle distribution in Jurkat cells at day 6 post-transfection with R7 and SMRwt peptide (panel A-1) or with R7 and SMRmt peptide (panel B-1).

DETAILED DESCRIPTION

Figure 1A:
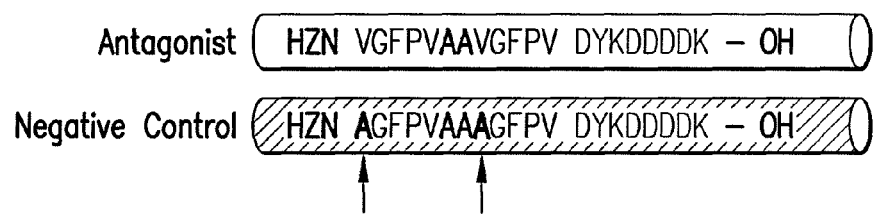
FIG. 1 is a composite of diagrams showing the synthetic HIV-1 NefSMRwt peptide (antagonist) and HIV-1 NefSM- Rmt peptide (negative control) (panel A); the vector constructs expressing HIV-1 NefSMRwt peptide fused with GFP or HIV-1 NefSMRmt peptide fused with GFP (panel B); and the amount of acetylcholinesterase, a marker for exosomes, in MDA-MB-231 cells transfected with either HIV-1 NefSMRwt peptide (panel C) or SMRmt peptide (panel D). Untransfected MDA-MB-231 cells were used as negative controls. The cells were cultured for 48 hours in serum-free medium. One ml of supernatant was spun at 400,000×g. Supernatant pellets or set volume of cell lysate were run on PAGE, blotted, and probed with anti-AchE mAb (Acetylcholinesterase—1:1000 dilution; marker for exosomes). The cell lysates were reprobed with anti-Tubulin mAb (1:4000). Bands were measured by densitometry, normalized against intracellular tubulin. Data shown here as percent relative to the untransfected control.
Figure 1B:
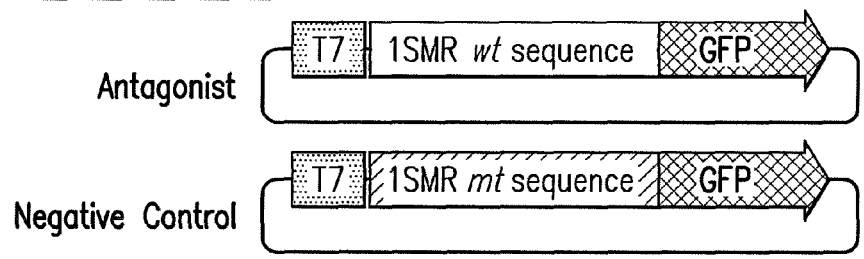
Figure 1C:
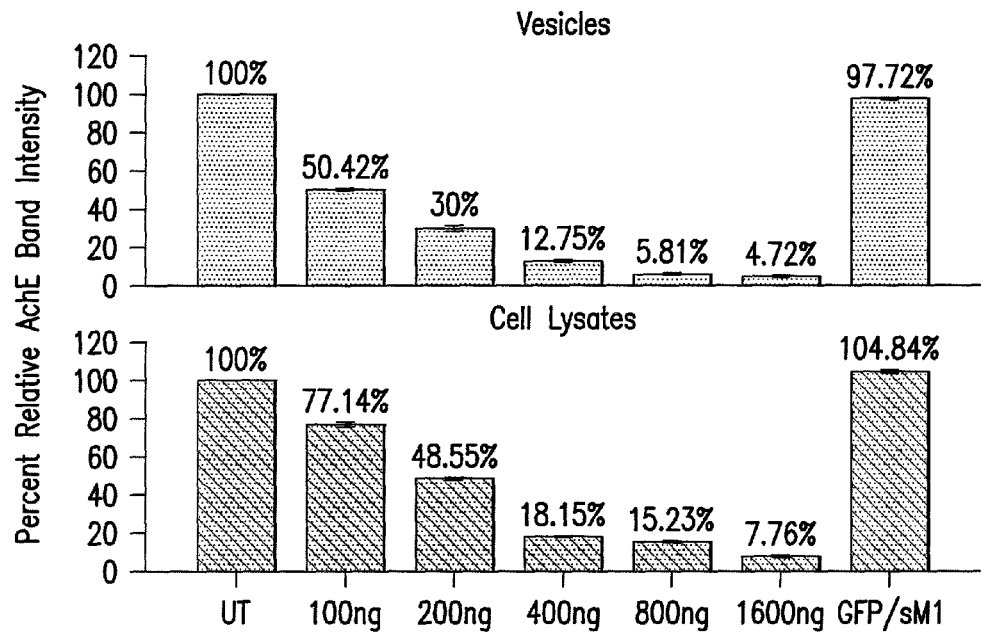
Figure 1D:
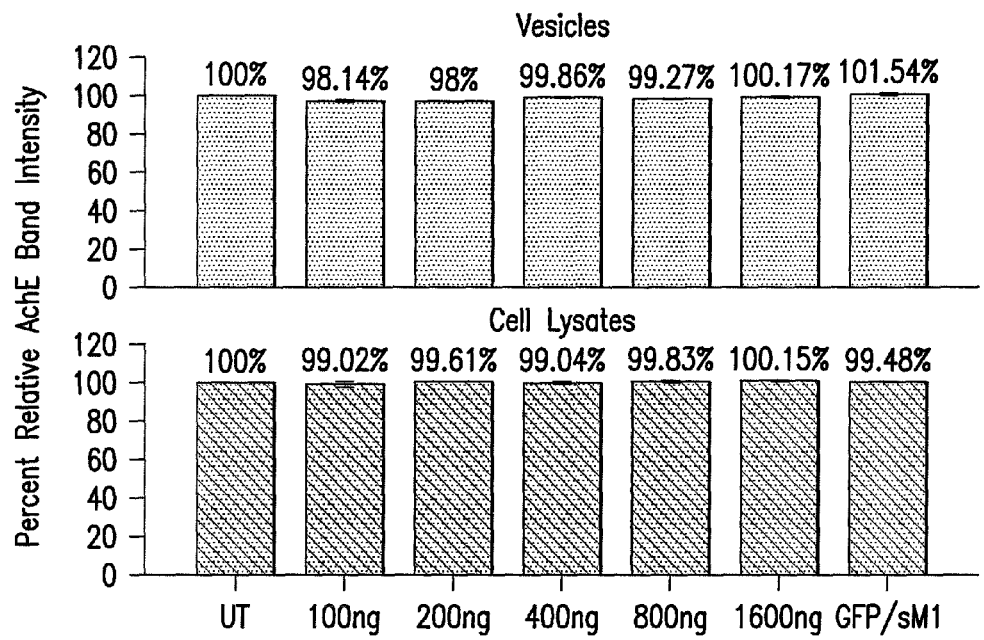

While this invention may be embodied in many different forms, there are described in detail herein specific preferred embodiments of the invention. This description is an exemplification of the principles of the invention and is not intended to limit the invention to the particular embodiments illustrated.

It is known that the cellular trafficking pathway is involved in the lifecycle of HIV and in tumor development (Grossman et al., (2002) Nat. Med. 8, 319-323). For example, the exosomes released by certain tumor cells dysregulate the immune system of the host, thus allowing growth and proliferation of the tumor. Currently, there is no practical technology to target the microparticle trafficking pathway and manipulate/inhibit microparticle release from cells. The present invention takes advantage of a HIV-Nef sequence that interacts with cellular factors and manipulates the trafficking pathway to block the cells ability to make microparticles.

Peptides

One aspect of the present invention relates to a novel peptide that inhibits the release of microparticles from cells. The peptide has a length of 10-100 amino acids and contains (1) at least one VGFPV (SEQ ID NO: 1) motif at the N-terminal, or (2) at least one VGFPV (SEQ ID NO: 1) motif at the C-terminal, or (3) at least two VGFPV (SEQ ID NO: 1) motifs. As used hereinafter, the term "microparticles" refers to microvehicles involved in cellular trafficking pathways. The microparticles are typically composed of a lipid bilayer containing a cytosolic fraction, and are generally less than 200 nm in diameter. Examples of microparticles include, but are not limited to exosomes, texosomes, and Tex or tumor exosomes.

In one embodiment, the peptide contains at least two SEQ ID NO: 1 motifs. In another embodiment, the peptide contains the amino acid sequence VGFPVAAVGFPV (SEQ ID NO: 2). In yet another embodiment, the peptide has the sequence of H2N-VGFPVAAVGFPVDYKDDDDK-OH (SEQ ID NO: 3).

The peptides of the present invention may be chemically synthesized or produced with recombination DNA technology (e.g., expressed and purified from host cells). Methods for synthesizing peptides or producing peptides by recombinant DNA technology are well known to one skilled in the art.

Expression Vectors

Another aspect of the present invention relates to a polynucleotide encoding the novel peptide of the present invention and an expression vector carrying a polynucleotide encoding the novel peptide of the present invention.

The term "expression vector" refers to a non-viral or a viral vector that comprise a polynucleotide encoding the novel peptide of the present invention in a form suitable for expression of the polynucleotide in a host cell. One type of non-viral vector is a "plasmid," which includes a circular double-stranded DNA loop into which additional DNA segments can be ligated. In the present specification, "plasmid" and "vector" can be used interchangeably as the plasmid is the most commonly used form of vector.

The expression vectors include one or more regulatory sequences, selected on the basis of the host cells to be used for expression, and operably linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, such as the novel peptide of the present invention.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences).

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

In one embodiment, the mammalian expression vector is capable of directing expression of the polynucleotide preferentially in a particular cell type (e.g., tissue-specific regulatory elements are used to express the polynucleotide). Tissue-specific regulatory elements are known in the art and may include epithelial cell-specific promoters. Other non-limiting examples of suitable tissue-specific promoters include the liver-specific promoter (e.g., albumin promoter), lymphoid-specific promoters, promoters of T cell receptors and immunoglobulins, neuron-specific promoters (e.g., the neurofilament promoter), pancreas-specific promoters (e.g., insulin promoter), and mammary gland-specific promoters (e.g., milk whey promoter). Developmentally-regulated promoters (e.g., the .alpha.-fetoprotein promoter) are also encompassed.

In another embodiment, the expression vectors are viral vectors. Examples of viral vectors include, but are not limited to, retroviral vectors, lentiviral vectors, adenoviral vectors, adeno-associated viral (AAV) vectors, herpes viral vectors, and alphavirus vectors. The viral vector can also be an astrovirus, coronavirus, orthomyxovirus, papovavirus, paramyxovirus, parvovirus, picornavirus, poxvirus, togavirus viral vector.

The expression vectors of the present invention may express the peptides of the present invention using a regulation expression system. Systems to regulate expression of therapeutic genes have been developed and incorporated into the current viral and nonviral gene delivery vectors. These systems are briefly described below:

Tet-on/off system. The Tet-system is based on two regulatory elements derived from the tetracycline-resistance operon of the *E. coli* Tn10 transposon: the Tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repressor (rtetR) fused to the VP16 activation domain of herpes simplex virus. The "reporter" plasmid contains a tet-responsive element (TRE), which controls the "reporter" gene of choice. The rtetR-VP16 fusion protein can only bind to the TRE, therefore activates the transcription of the "reporter" gene, in the presence of tetracycline. The system has been incorporated into a number of viral vectors including retrovirus, adenovirus and AAV.

Ecdysone system. The ecdysone system is based on the molting induction system found in Drosophila, but modified for inducible expression in mammalian cells. The system uses an analog of the drosophila steroid hormone ecdysone, muristerone A, to activate expression of the gene of interest via a heterodimeric nuclear receptor. Expression levels have been reported to exceed 200-fold over basal levels with no effect on mammalian cell physiology.

Progesterone system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GALA-binding site.

Rapamycin system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain has also been fused to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral and AAV vectors. Long term regulatable gene expression has been achieved in both mice and baboons.

The delivery of the expression vectors of this invention into cells can be achieved by infection (for viral vectors), transfection (for non-viral vectors) and other methods well known to one skilled in the art. Examples of other delivery methods and media include, polycationic condensed DNA linked or unlinked to killed viruses, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may also be employed. Briefly, DNA sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose or transferrin. Naked DNA may also be employed. Uptake efficiency of naked DNA may be improved using biodegradable latex beads. The method may be improved further by treatment of the beads to increase hydrophobicity and thereby facilitate disruption of the endosome and release of the DNA into the cytoplasm.

In certain embodiments, the novel peptide of the present invention is introduced in a target cell with one or more other drugs that inhibit secretion. Examples of such drugs include, but are not limited to, dimethyl amiloride, an inhibitor of the H+/Na+ and Na+/Ca2+ channels, and omeprazole, a K+/H+ ATPase inhibitor.

Pharmaceutical Composition

Another aspect of the present invention relates to a pharmaceutical composition for treating AIDS or tumors. The pharmaceutical composition comprises (1) a peptide containing at least one VGFPV (SEQ ID NO: 1) motif at the N-terminal and having a length of 10-100 amino acids or an expression vector encoding such a peptide, and (2) a pharmaceutically acceptable carrier.

In certain embodiments, the pharmaceutical composition further comprises one or more other drugs that inhibit secretion. In one embodiment, the one or more other drugs include dimethyl amiloride or omeprazole or both.

As used herein, the language "pharmaceutically acceptable carrier" is intended to include any and all solvents, solubilizers, fillers, stabilizers, binders, absorbents, bases, buffering agents, lubricants, controlled release vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdemial (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an SRPP or an anti-SRPP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the bioactive compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the therapeutic moieties, which may contain a bioactive compound, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form, as used herein, includes physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans The dosage of such compounds lies preferably within a range of circulating concentrations that includes the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Another aspect of invention includes methods for preparing pharmaceutical compositions for modulating the expression or activity of the peptide of the present invention. Such methods comprise formulating a pharmaceutically acceptable carrier with an agent which modulates expression or activity of the peptide of the present invention. Such compositions can further include additional active agents. Thus, the invention further includes methods for preparing a pharmaceutical composition by formulating a pharmaceutically acceptable carrier with an agent which modulates expression or activity of the peptide of the present invention and one or more additional bioactive agents.

Methods for Treating AIDS and Tumors

Another aspect of the present invention relates to a method for treating AIDS. The method comprises administering to a subject in need of such treatment an effective amount of a peptide containing at least one VGFPV motif and having a length of 10-100 amino acids.

In one embodiment, the peptide contains at least two VGFPV (SEQ ID NO: 1) motifs. In another embodiment, the peptide contains the amino acid sequence VGFPVAAVGFPV (SEQ ID NO: 2). In yet another embodiment, the peptide has the sequence of H2N-VGFPVAAVGFPVDYKDDDDK-OH (SEQ ID NO: 3).

Another aspect of the present invention relates to a method for treating tumors. The method comprises administering to a subject in need of such treatment an effective amount of a peptide containing at least one SEQ ID NO: 1 motif at the N-terminal and having a length of 10-100 amino acids.

In one embodiment, the peptide contains at least two SEQ ID NO: 1 motifs. In another embodiment, the peptide contains the amino acid sequence SEQ ID NO: 2. In yet another embodiment, the peptide further comprises the sequence of H2N-VGFPVAAVGFPVDYKDDDDK-OH (SEQ ID NO: 3).

The present invention is further illustrated by the following examples which should not be construed as limiting. The contents of all references, patents and published patent applications cited throughout this application, as well as the Figures and Tables are incorporated herein by reference.

Example 1

Inhibition of Vesicle Secretion in Tumor Cells 1-1. Cells and Cultures

MDA-MB-231 cells were derived from human breast adenocarcinoma and human breast carcinoma cells, respectively, and were obtained from the American Type Culture Collection (Manassas, Va.). Cells were sustained in RPMI 1640 medium (Invitrogen, Palo Alto, Calif.) supplemented with streptomycin (100 U/ml), penicillin (100 U/ml), L-glutamine (2 mM), and HEPES buffered saline solution (30 µM).

1-2. Antibodies

The following antibodies were used: (i) a mouse monoclonal (MEM-28) anti-CD45 antibody (Abcam, Inc, Cambridge, Mass.); (ii) a murine monoclonal anti-HIV-1 Nef antibody (ImmunoDiagnostic, INC., Ma.); (iii) a monoclonal anti-Acetylcholinesterase (AchE) antibody, clone AE-1 (CHEMICON, Ca.); (iv) an monoclonal anti-Tubulin antibody, clone B-5-1-2 (SIGMA, Mo.) and (v) an goat anti-mouse IgG heavy plus light chains (H+L) labeled with horseradish Peroxidase (Pierce, Rockford, Ill.).

1-3. Exosomes Isolation and Purification from Mda-MB-231 Cells

MDA-MB-231 cells ($3\times10^5$) were transfected with SMRwt (H2N-VGFPVAAVGFPVDYKDDDDK-OH) (SEQ ID NO: 3), SMRmt (H2N-AGFPVAAAGFPVDYKDDDDK-OH) (SEQ ID NO: 4), pQBI-SMRwt-GFP (FIG. 1, panel B) or pQBI-SMRmt-GFP (FIG. 1, panel B) by Chariot™ methods (Active Motif co., Carlsbad, Calif.). The two peptides were made commercially (FIG. 1, panel A). The SMR sequence is repeated twice at the N-terminal end of the peptide with a short dialanine separating the repeats. Following the SMR sequences is a c-terminal FLAG sequence that allows us to retrieve the peptide. However, any sequence could be inserted at the c-terminus The pQBI-SMRwt-GFP (SEQ ID NO: 5) and pQBI-SMRmt-GFP (SEQ ID NO: 6) constructs were generated by inserting a single copy of the SMR wt sequence or SMR mt sequence, respectively, between the T7 promoter and the GFP coding sequence of the pQBI vector (Qbiogen Inc.)

Briefly, 1 µg of peptides were added into 200 µl serum-free medium with 10 µl Chariot solution, mixed well, and incubated at room temperature for 30 min. The cell cultures plate was washed. 400 µl of Chariot™/DNA/Peptide complex was added into the plate, followed with 1600 µl serum-free medium. The cells were incubated with 5% CO2 at 37° C. for 1 hr, 1 ml of complete growth medium was added into the plate and the plate was incubated at 37° C. with 5% CO2 for 48 hr. The cells were removed from the culture supernatant by centrifugation at 2000×g for 5 min. The supernatant was then subjected to spin at 10,000 g for 30 min to remove cell debris, 1 ml of the 10,000 g supernatant was placed into a centrifuge tube and spun at 50,000×g, 100,000×g and 400,000×g for 2 hr at 4° C. to pellet exosomes. Similarly prepared supernatants from untransfected MDA-MB-231 cells were used as negative controls.

1-4. Immunoblot Analysis

Pellets were resuspended in 1×SDS-PAGE loading buffer, separated by SDS-PAGE. Twenty microliters of each sample was separated by SDS-PAGE on a 4-20% Tris-HCl Criterion precast gel (Bio-Red Laboratories, Hercules, Calif.), and electrophoretically transferred to a nitrocellulose membrane. The membrane was washed in TBS for 5 min, and then blocked with 5% non-fat milk in TTBS (TBS with 0.1% Tween 20) for 1 h by shaking at room temperature and processed for immunoblotting using the primary antibody (anti-acetylcholine esterase (AchE) mAb at 1:1000 dilution) by shaking at 4° C. for overnight, followed by HRP-conjugated IgG Ab (H+L). Protein bands were detected by Western Blotting Luminol Reagent (Santa Cruz Biotechnology, Inc., Santa Cruz, Calif.). After detection of AchE, the blot was stripped and re-hybridized with CD45. Protein bands were detected by Western Blotting Luminol Reagent, followed by exposure to photographic film (BioMax film; Fisher Scientific, Pittsburgh, Pa.). Images were scanned into Adobe Photoshop 6.0, and arranged via Adobe Illustrator software (version 8.0; Adobe Systems) and densitometry was performed using Scion Image J software, Release Beta 3b (Scion Corporation, Frederick, Md.)

As shown in FIG. 1, antagonist peptide (HIV-1 NefSM-Rwt; FIG. 1, panel C) knocked down AChE intracellularly and in the cell supernatant (measure of secretion of tumor vesicles) from MDA-MB-231 cells. The data also displays a dose dependency in both compartments. Negative control (HIV-1 NEfSMRmut, FIG. 1, panel D) had no effect on AChE in either intracellular or supernatant compartments.

The above results show that the HIV-1 NefSMRwt peptide antagonizes the release of exosomal vesicles from tumor cells. These vesicles have been shown to dysregulate the immune system in cancer patients allowing tumors to survive and thrive. Antagonism of exosome release would allow the immune system to repair itself and attack/kill the tumors.

Example 2

Vesicle Secretion Inhibition 1N HIV-1 NEF Transfected Cells

While the genetic studies clearly showed that mutating the SMR motif abolished Nef secretion, it was not clear whether this effect was due to the disruption of a SMR-binding site, or simply a structural change leading to Nef protein misfolding. Therefore, a set of co-transfection experiments were performed. HEK293 cells were co-transfected with 0.5 µg of pQBI-HIV Nef-GFP (expresses wild type Nef protein) and either 0.5 µg of HIV-1 Nef SMRwt or SMRmut peptide or sM1 peptide (a totally random control peptide, ALAETC-QNAWA (SEQ ID NO: 7)) with Chariot. Briefly, the wild-type Nef-GFP clone and the SMR peptides were complexed with Chariot reagent for 30 minutes at RT. The DNA/peptide/Chariot complex was added to HEK293 cells in serum-free media, and the cells were plated. Following incubation for 2 hours at 37° C., media with serum was added to the dish, and the cells were incubated at 37° C. for 48 h. The media was then collected and assayed for secretion using a spectrofluorimeter. The conditioned supernatants from these cultures were assayed for GFP fluorescence by plate reader. The results are displayed in percent relative to the NefGfP+sM1 peptide (negative control; 100%) fluorescence.

Figure 2:
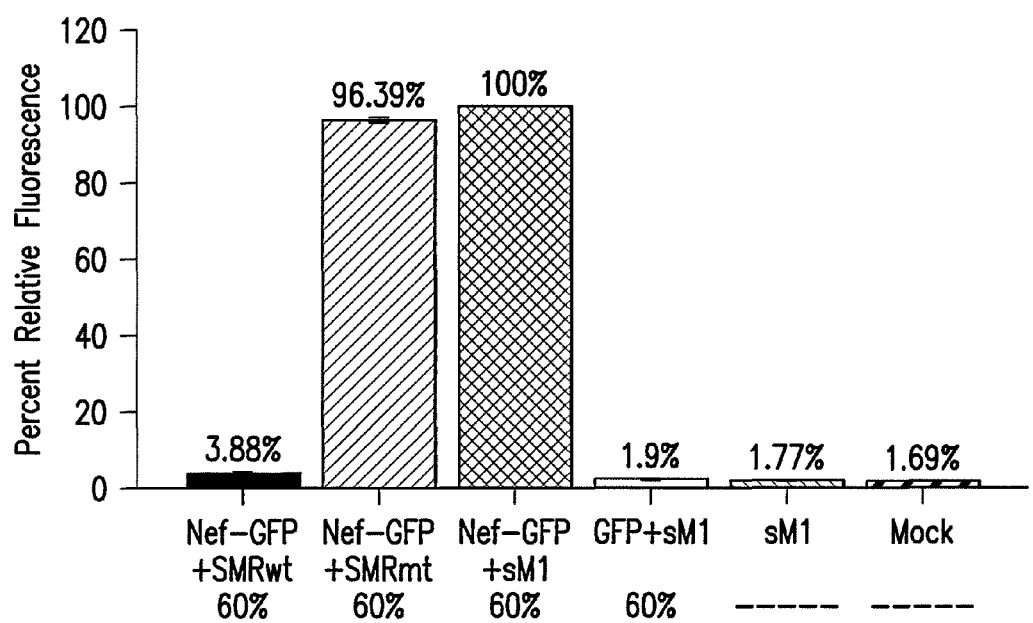
FIG. 2 is a diagram showing that the HIV-1 NefSMRwt peptide antagonizes the release of NefGFP in HEK293 cells.

As shown in FIG. 2, the HIV-1 NefSMRwt peptide (first bar from left) antagonizes the release of NefGFP into the extracellular supernatant. It has been shown that NefGFP is in the exosome like vesicles in the extracellular supernatant. The negative controls HIV-1 NefSMRmut and sM1 had no effect on vesicle release.

These results demonstrate that the antagonist blocks release of HIV-1 Nef transfected cells. The data suggest that these vesicles, similarly to those released the tumor cells, kill or dysregulate the immune system allowing HIV to thrive and eventually lead to AIDS pathogenesis. Antagonism of exosome release would allow the immune system to repair itself blocking progression to AIDS.

Figure 3A:
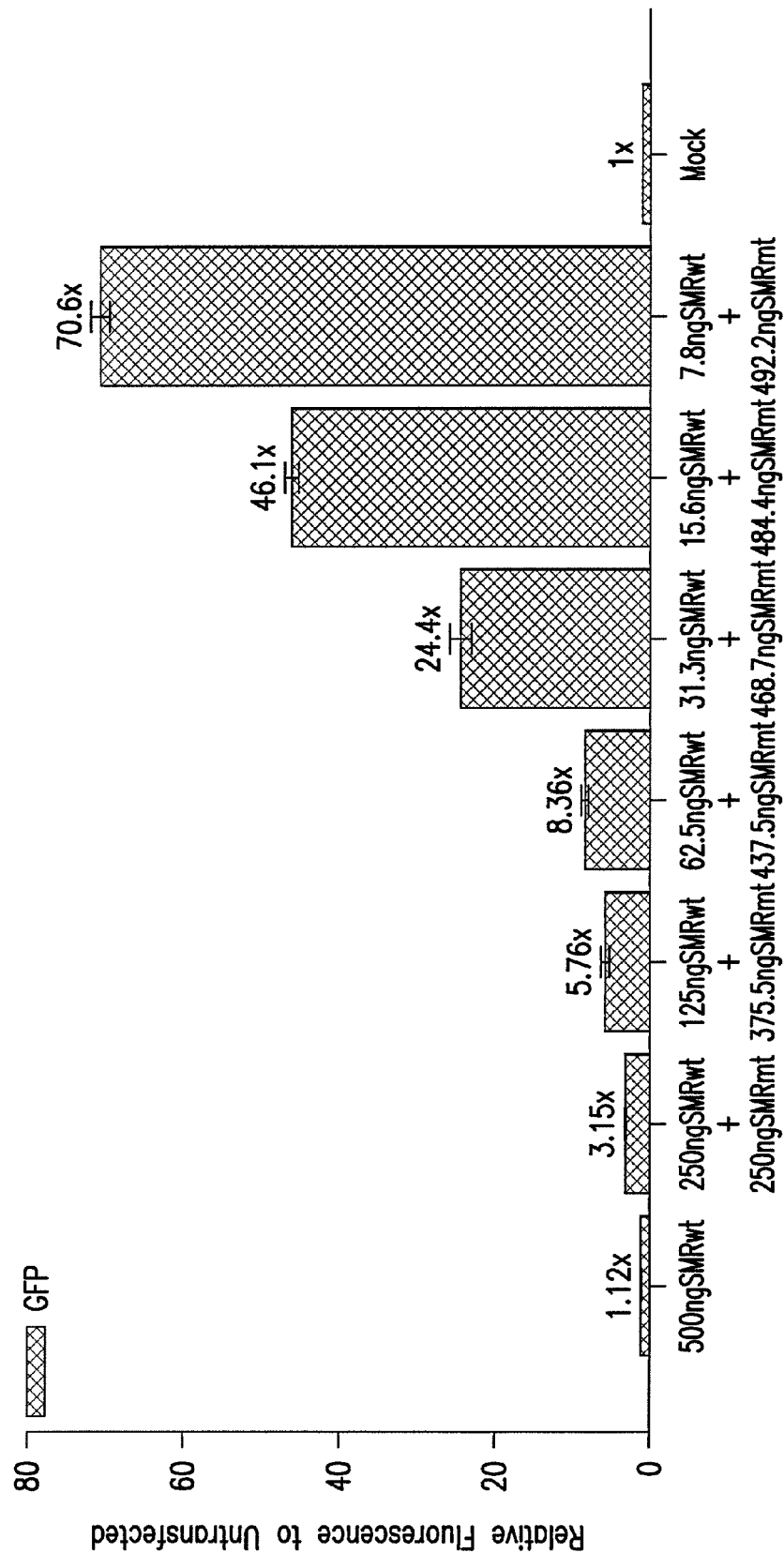
FIGS. 3A and 3B are diagrams showing that the HIV-1 NefSMRwt peptide antagonizes the release of NefGFP in Jurkat cells.
Figure 3B:
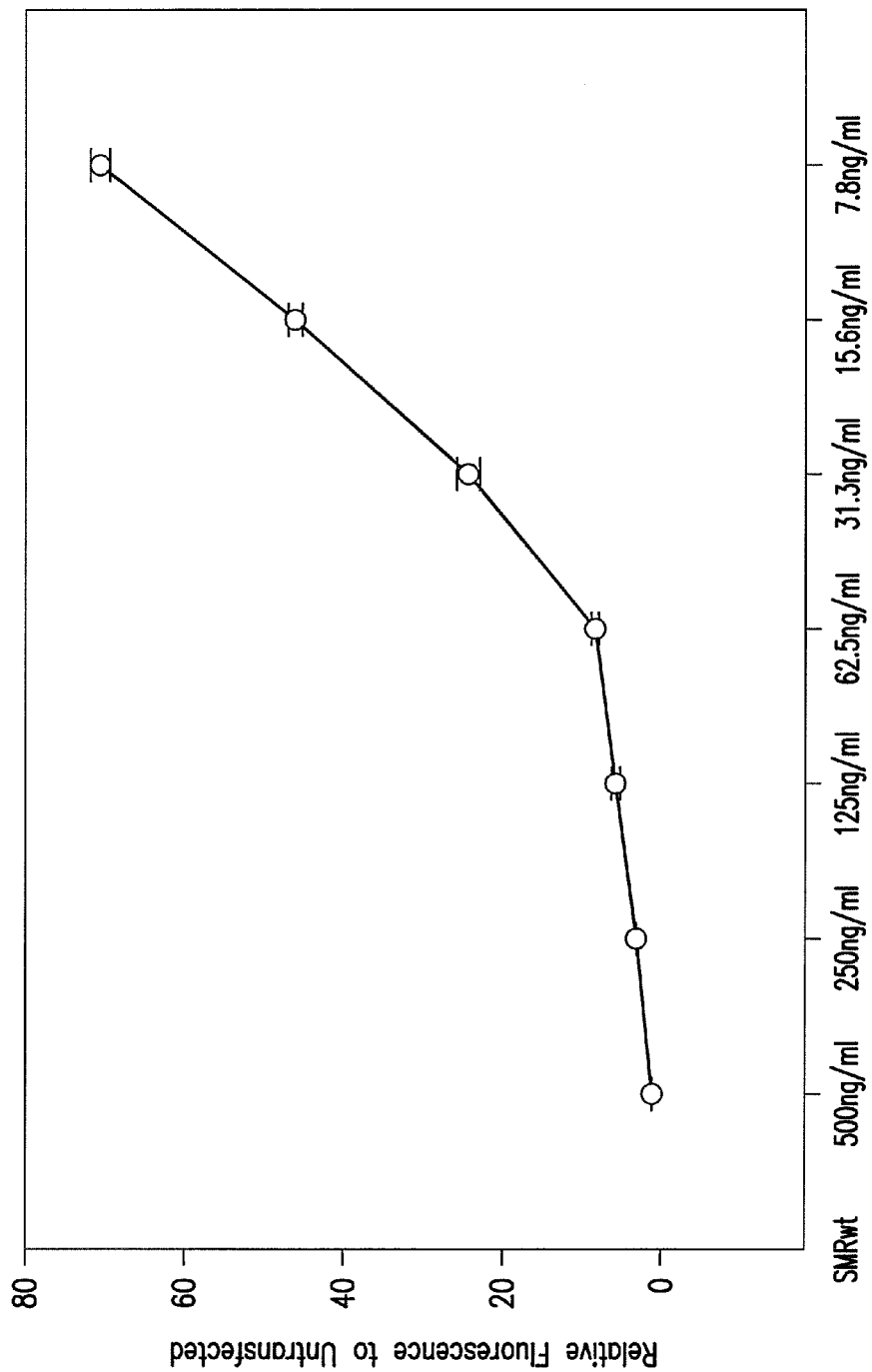

In another experiment, Jurkat cells were co-transfected with 500 ng HIV-1wtNef-GFP and 7.8-500 ng of SMRwt peptide by Chariot. As shown in FIG. 3A the SMRwt peptide inhibits the vesicle secretion in Jurkat cells. FIG. 3B is a dose-response curve showing that the SMRwt peptide inhibits the vesicle secretion in Jurkat cells in a dose-dependent manner.

Example 3

Inhibition of Vesicle Secretion and Virion Particle Release from HIV Infected Cells

3.1 Experiment I

I. Jurkat cells were co-transfected as shown below: (transfection efficiency 30-40% by Chariot Kit):

| | |
|---|---|
| #1. pNL4-3 + Nef SMR wt (antagonist) | 4 plates |
| #2. pNL4-3 + Nef SMR mt (nonfunctional antagonist) | 4 plates |
| #3. pNL4-3 + sM1 (negative control peptide) | 4 plates | pNL4-3 is a clone containing the viral genome. Transfection into cells allows expression of the viral genome and ultimately virion formation and release. The amount of virion production in the extracellular supernatant is measured through p24 protein (viral protein). Samples were collected at 48 hours and 96 hours post-infection.

At 48 hr postinfection two plates in each group were removed and analyzed by:
 a. p24 assay
 b. Nef assay
 c. Infectivity assay At 96 hr postinfection the other two plates in each group were removed and analyzed by:
 a. p24 assay
 b. Nef assay
 c. Infectivity assay As shown in Table I, the amount of virus production is reduced drastically at 96 hours in the presence of the peptide antagonist (NefSMRwt) with no effect seen for the negative control peptide (NefSMRmut). The Data suggest that the antagonist blocks production and/or release of virus particles from infected cells.

TABLE 1

Results of Experiment I

| Cells | Time | Sample | p24 pg/ml | Effect (a/b) |
|---|---|---|---|---|
| Jurkat | 48 hr | pNL4-3 + NefSMRwt (a) | 0 | 1 |
| | | pNL4-3 + NefSMRmut (a) | 0 | 1 |
| | | pNL4-3 + sM1 (b) | 0 | 1 |
| Jurkat | 96 hr | pNL4-3 + NefSMRwt (a) | 0 | <0.033 |
| | | pNL4-3 + NefSMRmut (a) | 15 | 0.5 |
| | | pNL4-3 + sM1 (b) | 30 | 1 |
| 293 | 48 hr | pNL4-3 + NefSMRwt (a) | 90 | 2 |
| | | pNL4-3 + NefSMRmut (a) | 30 | 0.67 |
| | | pNL4-3 + sM1 (b) | 45 | 1.0 |
| 293 | 96 hr | pNL4-3 + NefSMRwt (a) | 345 | 0.359 |
| | | pNL4-3 + NefSMRmut (a) | 1125 | 1.17 |
| | | pNL4-3 + sM1 (b) | 960 | 1 |

3.2 Experiment II

Jurkat cells, HEK293 cells, THP-1 monocytes and U937 monocytes were co-transfected with either R7 or Nef SMR wt (antagonist) or with R7+Nef SMR mt (nonfunctional antagonist) by Chariot™ Kit. The transfection efficiency was 30-40%.

R7 is a clone containing the viral genome. Transfection into cells allows expression of the viral genome and ultimately virion formation and release. The amount of virion production in the extracellular supernatant is measured through p24 protein (viral protein).

At 2 hours, 3 days, 6 days, 9 days, 13 days, 15 days, 17 days, 20 days, 23 days, 27 days and 36 days post-transfection, 0.5 ml supernatant were collected from each plate, mixed with 0.5 ml fresh media and analyzed by p24 ELISA assay. 1.5 ml of supernatant were collected from each plate and spun in a TLA100 rotor at 400,000×g for 1 hour to create the pellets. The pellets were used for Western blot analysis with p24 mAb and Nef mAb.

Figure 4A:
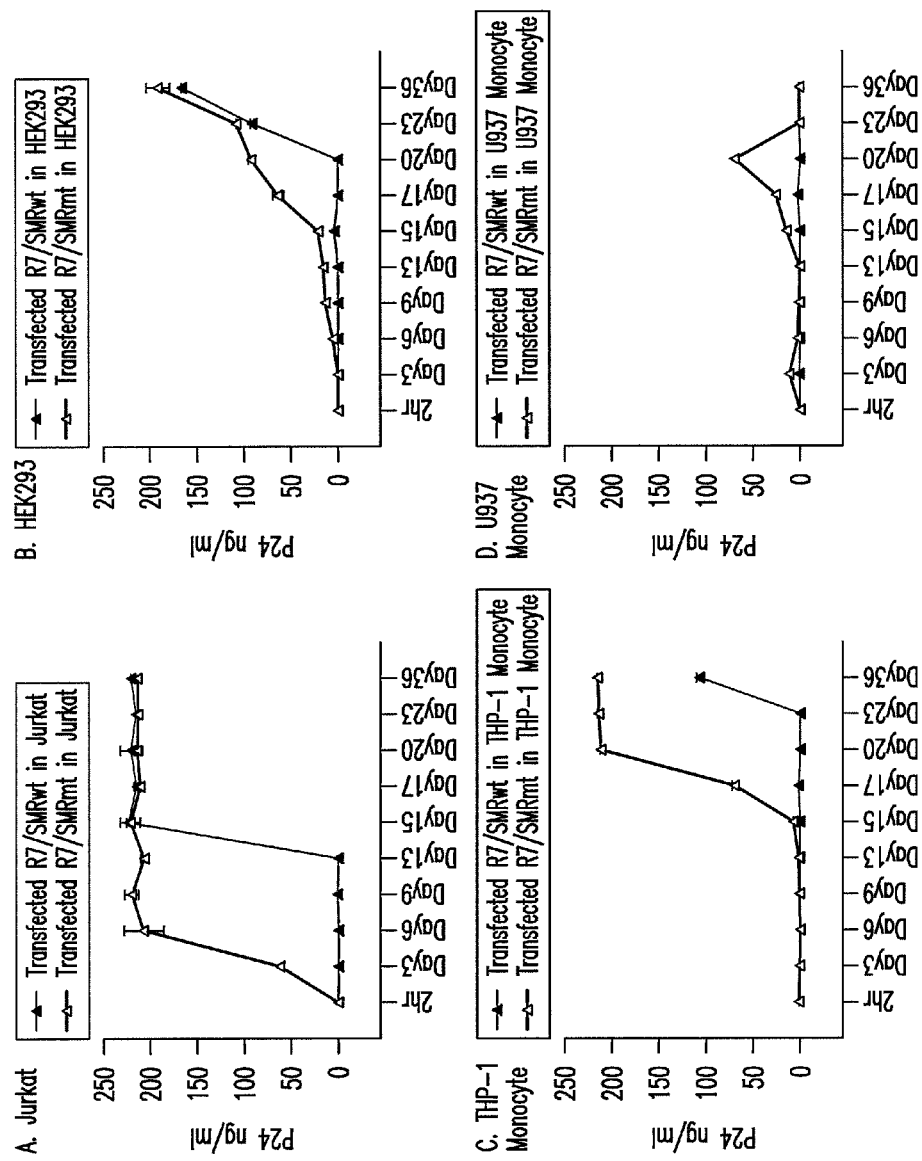
FIG. 4A is a composite of diagrams showing ELISA analysis of p24 concentration in Jurkat cells (panel A), HEK293 cells (panel B), THP-1 Monocytes (panel C) and U937 monocytes (panel D).
Figure 4B:
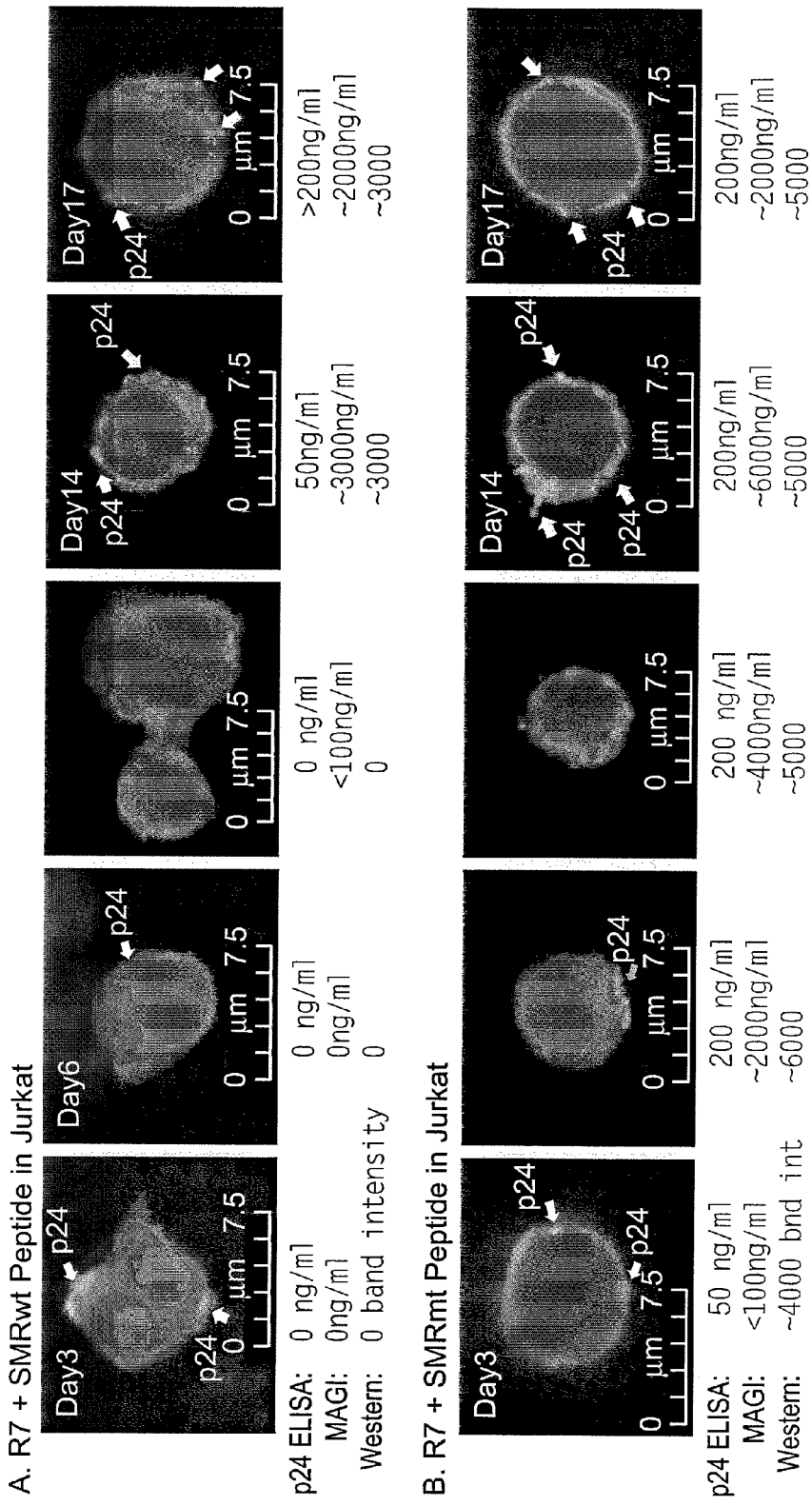
FIG. 4B is a composite of confocal microscope pictures showing blocking of p24 release in Jurkat cells by SMRwt peptide (panel A) but not by SMRrmt peptide (panel B).

As shown in FIG. 4A, the p24 concentrations increased in Jurkat cells 3 days post transfection in the negative control (R7/SMRmt) but did not increase in SMRwt (antagonist) cultures until 13 days post transfection. Similar results were also observed in HEK293 cells and in THP-1 monocytes. There is little p24 in SMRwt transfected U937 monocytes, suggesting that the cells could not eliminate the SMRwt antagonist. These data suggest that SMRwt antagonizes some aspect of viral growth or viral release from infected cells. The effect of SMRwt, however, seems to be temporary. It appears that Jurkat and HEK cells can degrade the peptide over time, while U937 monocytes cannot degrade the peptide. The temporary effect of the peptide may be overcome by using non-degradable peptide (e.g., peptides with sulfur bond, or d-enatomer peptides). FIG. 4B is a composite of confocal microscopic pictures at day 3, 6, 10, 14, 17 after transfection showing the blockage of p24 release by R7/SMRwt (panel A) but not by R7/SMRmt (panel B) in Jurkat cells. The result matched with data obtained from ELISA/Western/ and MAGI analysis. Blue stain is a nuclear stain, Red stain is cytoplasmic stain, and Green FITC stain is for HIV p24 protein. The p24 can be seen heavily accumulating in the cytoplasm of antagonist treated cells in day 3, 6, 10 images as compared to negative control treated cells in same images. In day 14 and 17, the p24 begins to look like that in the negative control treated images. This matches the fact that the p24 appears to be released in the MAGI/Western/ELISA data as we think the intracellular levels of the peptide are depleted allowing the virus to begin to be released.

Figure 4D:
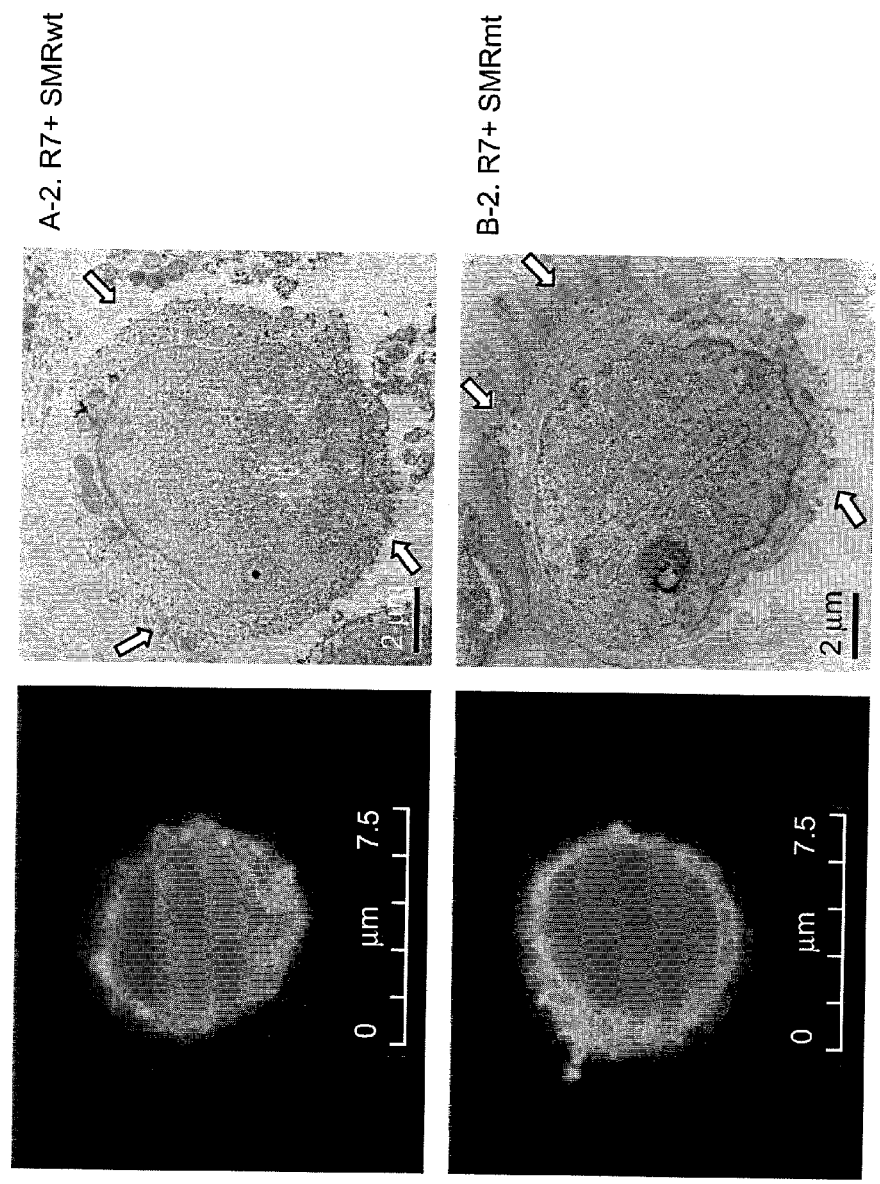
FIG. 4D is a composite of confocal and electron microscope pictures showing viral particle distribution in Jurkat cells at day 14 post-transfection with R7 and SMRwt peptide (panel A-2) or with R7 and SMRmt peptide (panel B-2)
Figure 4E:
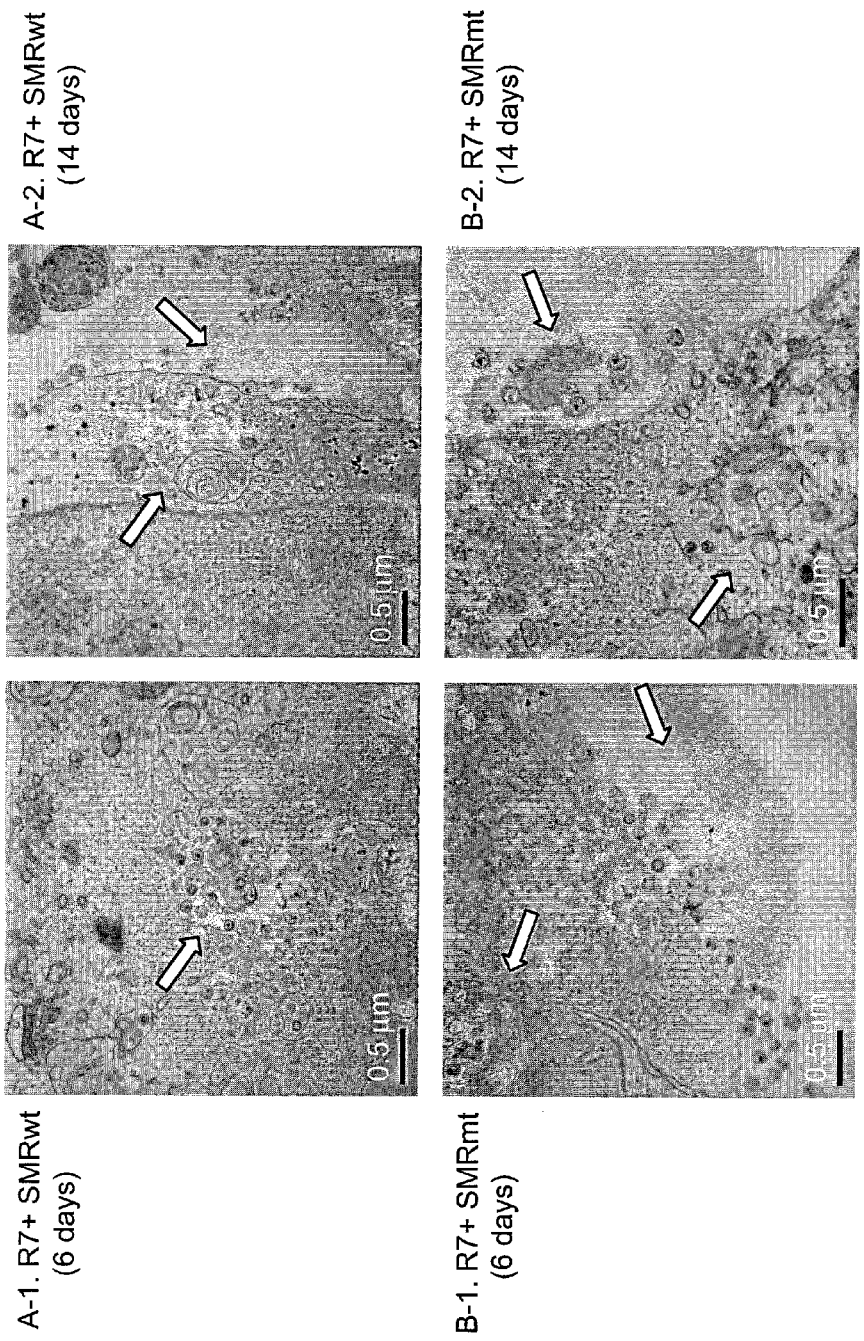
FIG. 4E is a composite of confocal and electron microscope pictures showing viral particle distribution in subcellular structures in Jurkat cells at day 6 post-transfection with R7 and SMRwt peptide (panel A-1) or with R7 and SMRmt peptide (panel B-1) in Jurkat cells and at day 14 post-transfection with R7 and SMRwt peptide (panel A-2) or with R7 and SMRmt peptide (panel B-2) in Jurkat cells.
Figure 5:
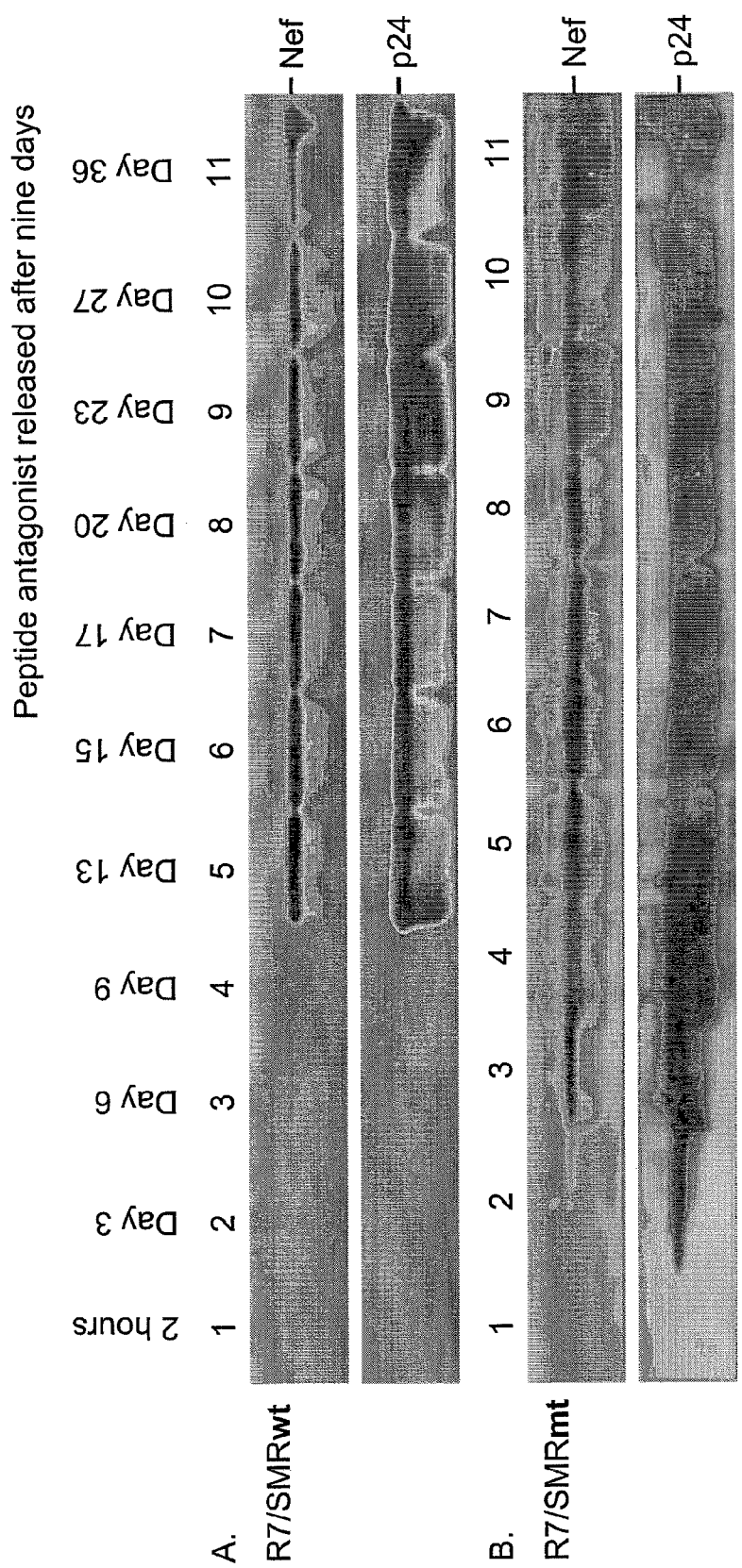
FIG. 5 is a composite of pictures showing the Western blot analysis of Nef and p24 in Jurkat cells transfected with R7/SMRwt (panel A) or R7/SMRmt (panel B).
Figure 6:
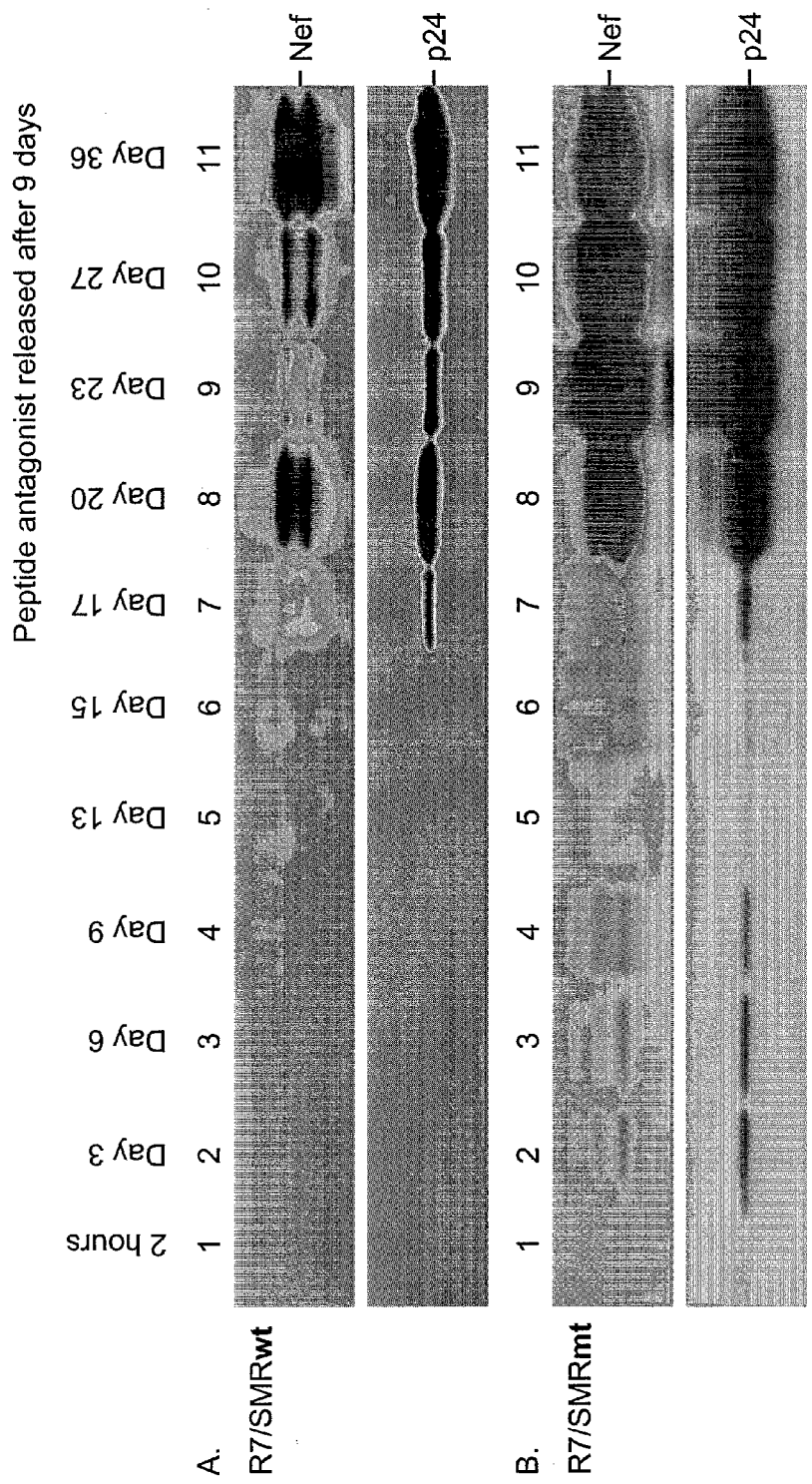
FIG. 6 is a composite of pictures showing the Western blot analysis of Nef and p24 in HEK293 cells transfected with R7/SMRwt (panel A) or R7/SMRmt (panel B).
Figure 7:
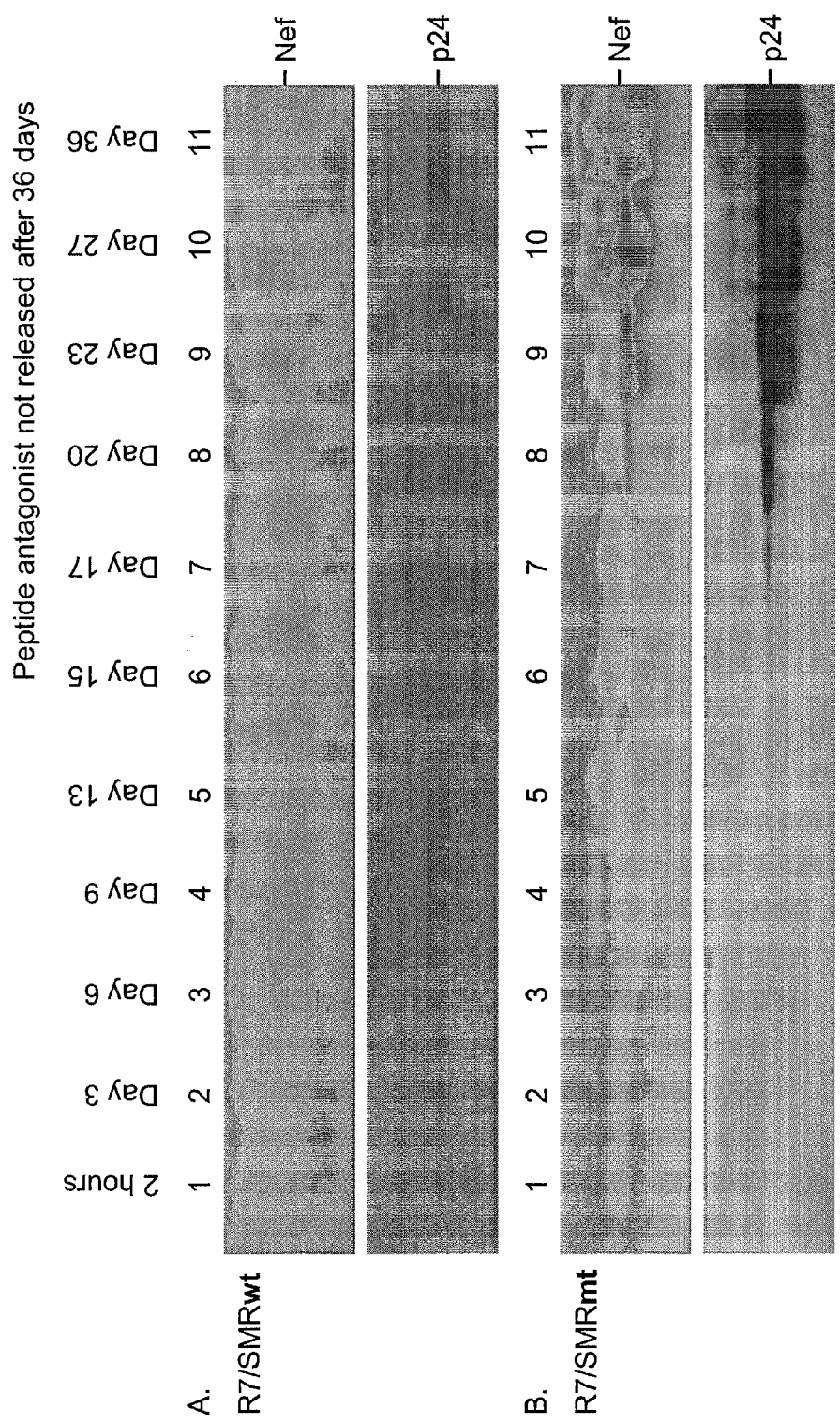
FIG. 7 is a composite of pictures showing the Western blot analysis of Nef and p24 in THP-1 monocyte transfected with R7/SMRwt (panel A) or R7/SMRmt (panel B).
Figure 8:
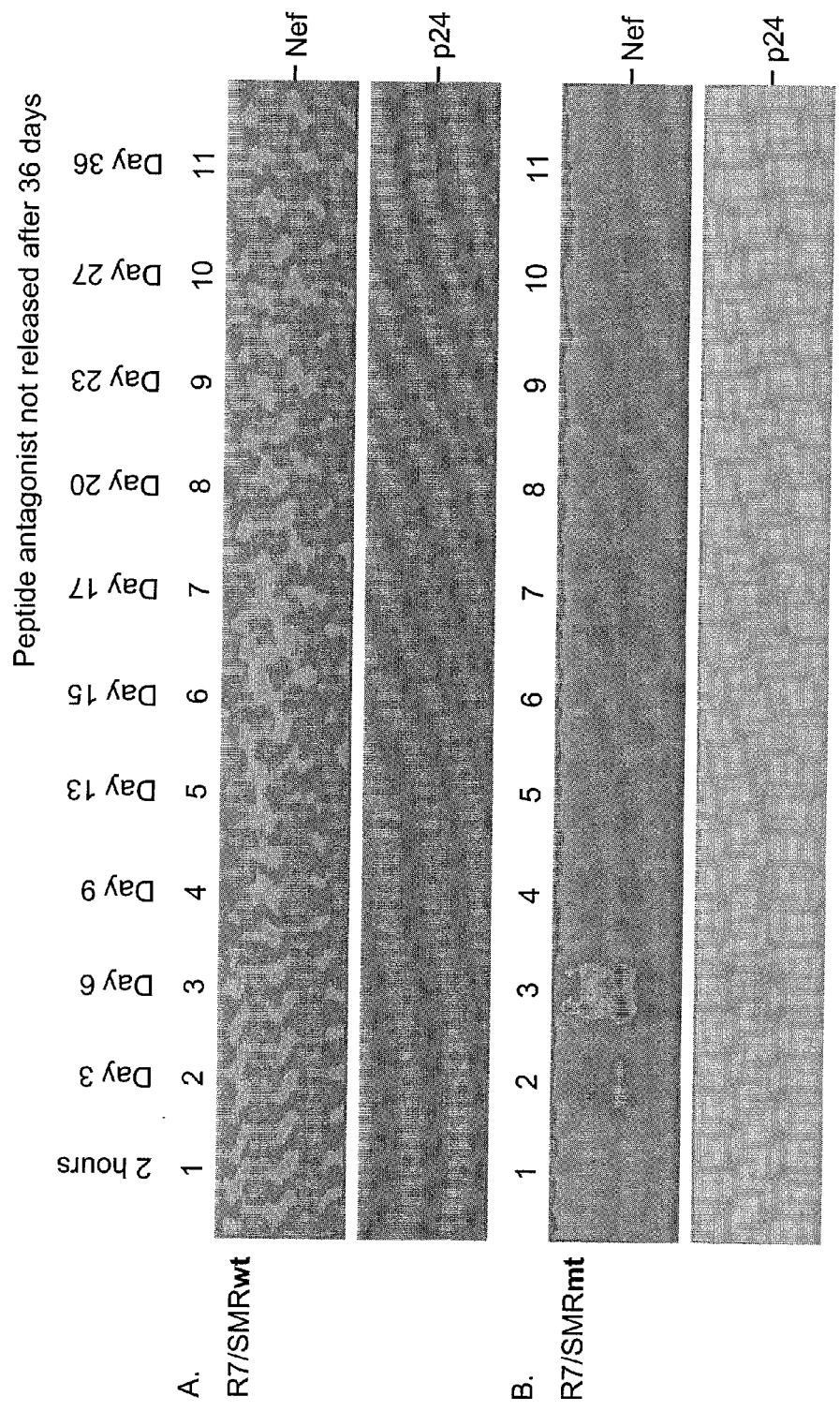
FIG. 8 is a composite of pictures showing the Western blot analysis of Nef and p24 in U937 monocyte transfected with R7/SMRwt (panel A) or R7/SMRmt (panel B).
Figure 9:
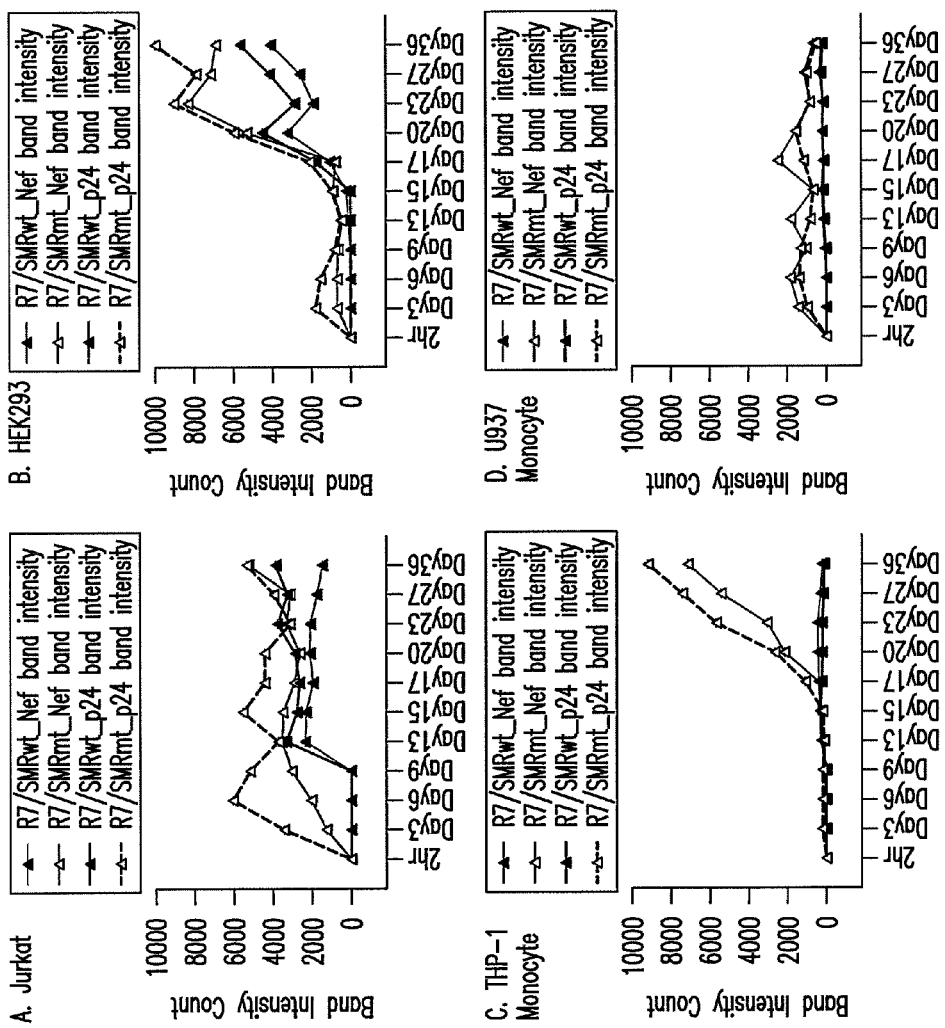
FIG. 9 is a composite of diagrams showing Western blot analysis of Nef and p24 in Jurkat cells (panel A), HEK293 cells (panel B), THP-1 Monocytes (panel C) and U937 monocytes (panel D).

FIGS. 4C-4E are electron microscopic pictures showing Jurkat cells transfected with R7/SMRwt or R7/SMRwt at day 6 (FIG. 4C) and day 14 (FIG. 4D) post transfection. On day 6, viral particles or nucleocapsid can be observed accumulating in to cytoplasm and within the MVBs inside the cells treated with R7/SMRwt. No viral particles can be observed accumulating on the extracellular surface of these cells (FIG. 4C, panel A-1 and). In contrast, very few MVBs can be observed inside the cell treated with R7/SMRmt, with most of the viral particles observed accumulating on the extracellular surface of the cell and polarized on the southern pole of the cell (FIG. 4C, panels B-1). On day 14, viral particles can be observed accumulating on the extracellular surface of the cell treated with R7/SMRwt (FIG. 4D, panel A-2) nonpolarized across the entire membrane surface, very much as observed in cells treated with R7/SMRmt, the negative control (FIG. 4D, panel B-2). Higher magnification images are shown in the following pictures of both six and 14 day antagonist and negative control peptide images to show the electron dense 'viral particles' accumulating as described above (FIG. 4E). The evidence shows that the SMRwt antagonist delays release of virus from infected cells as measured by EM.

The results of the Western blot analysis are shown in FIGS. 5-8. The results are summarized in FIG. 9. As shown in FIGS. 3-9, the amount of virus production in the presence of the peptide antagonist (NeISMRwt) is drastically reduced to zero or close to zero. No effect is observed for the negative control peptide (NefSMRmut). Assays of the cell lysates show that the production of p24 is the same in all assay conditions suggesting no effect on viral protein expression. The data suggest that the antagonist blocks release of virus particles from infected cells. This is possibly due to antagonism of trafficking of viral component(s) to the cytoplasmic membrane. Ultimately this would (i) shutdown the HIV infection and (ii) block progression to AIDS.

3.3 Experiment III

Figure 10:
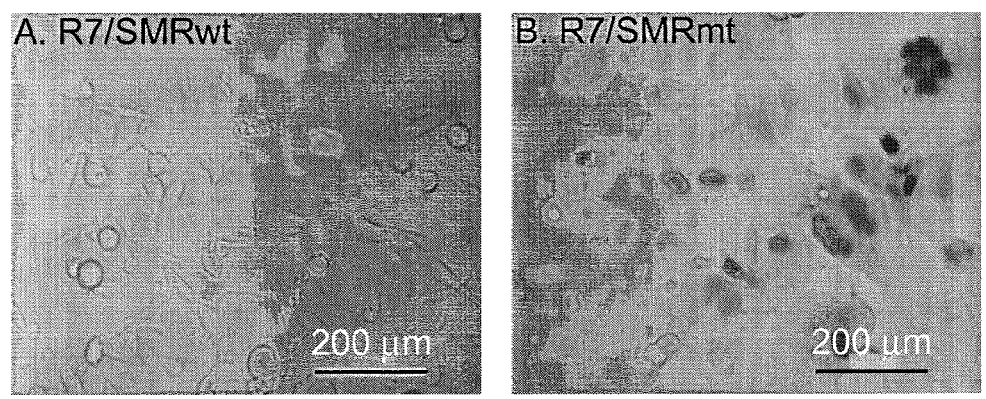
FIG. 10 is a composite of pictures of Magi/CXCR4 cells transfected with either R7 viral DNA/SMRwt peptide (panel A) or R7 viral DNA/SMRmt peptide (panel B).

Magi/CXCR4 cells were exposed to 48 hour conditioned supernatants from Jurkat cells, HEK293 cells, THP-1 monocytes, or U937 monocytes transfected with either R7 viral DNA/SMRwt peptide or R7 viral DNA/SMRmt peptide. These cells were then fixed and stained with X-Gal. FIG. 10A shows Magi/CXCR4 cells exposed to a 1 ng/ml dilution of p24 supernatant from Jurkat cells transfected with R7/SMRwt. FIG. 10B shows Magi/CXCR4 cells exposed to a 1 ng/ml dilution of p24 supernatant from Jurkat cells transfected with R7/SMRmt. Cells productively infected with R7 are easily visualized under light microscopy by their blue nuclear staining. Magnification ×20. Note the cells treated with R7 and the peptide antagonist (SMRwt) display drastically reduced numbers of blue staining cells, while the cells treated with R7 and the negative control peptide (SMRmt) display many blue staining cells. This is indicative of virus in the conditioned supernatant from the R7/negative control peptide treated cells and no virus in conditioned supernatant from the R7/antagonist treated cells.

Figure 11:
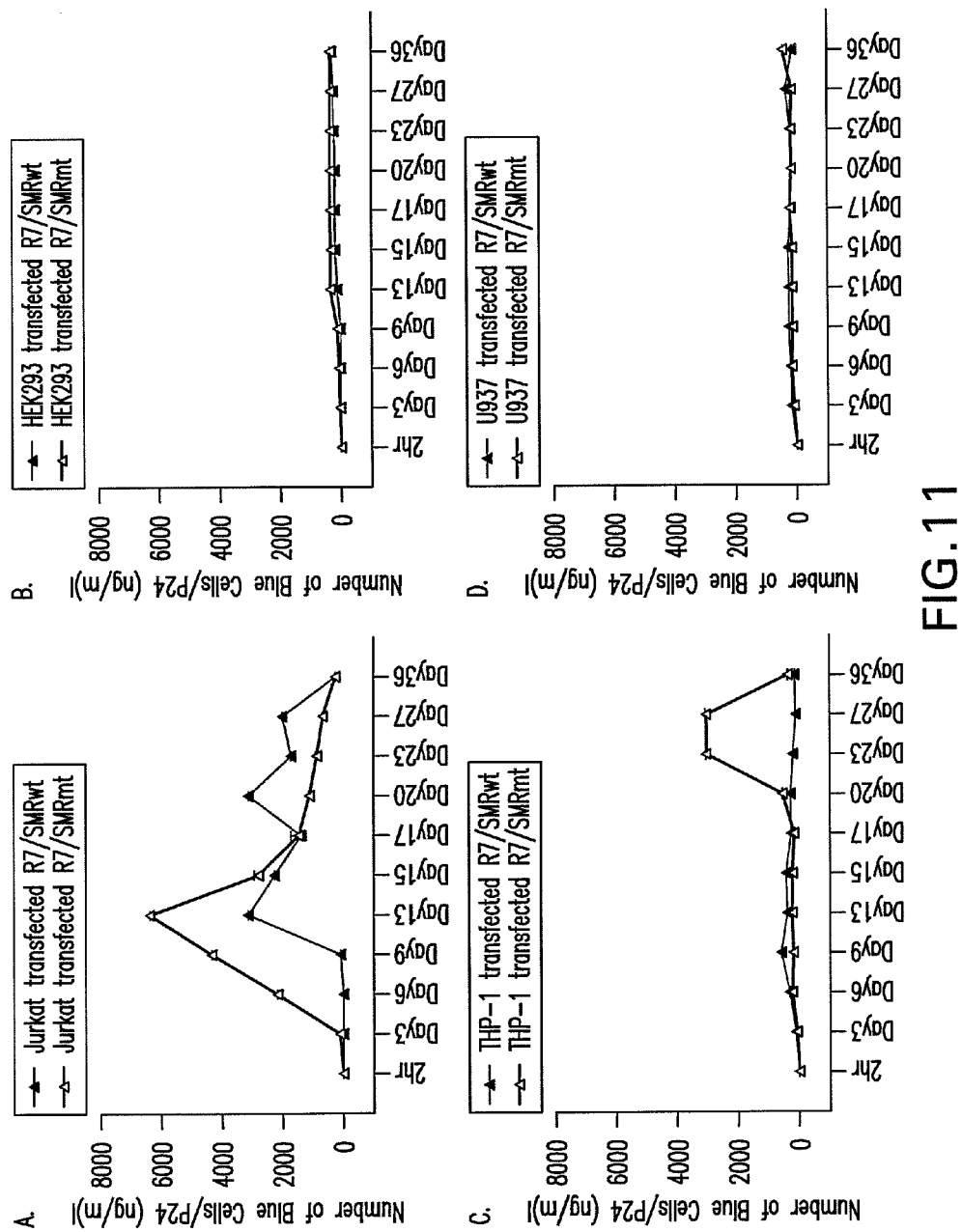
FIG. 11 is a composite of diagrams showing Magi assay viral infectivity in Jurkat cells (panel A), HEK293 cells (panel B), THP-1 Monocytes (panel C) and U937 monocytes (panel D).

These Magi cultures were quantitated for blue staining cells. The data was plotted as a function of time post-transfection. As shown in FIG. 11, the numbers of infected cells in the presence of the supernatant from NefSMRwt transfected Jurkat cells or NefSMRwt transfected THP-1 monocytes are significantly reduced. The data suggest that the antagonist blocks release of virus particles from infected cells. This is possibly due to antagonism of trafficking of viral component(s) to the cytoplasmic membrane. Ultimately this would shutdown the HIV infection and block progression to AIDS.

In summary, these experiments demonstrate that this technology could be used to force cells to make and extracellularly secrete any protein or epitope, so that the protein or epitope can be easily purified from the cells. The vesicles could also be used for chemotherapy if loaded with a targeting epitope (e.g., antibody epitope to a tumor marker) and an antitumor protein or epitope. Further, with this technology the vector could be transfected into the specific patient cells so as to be using self-vesicles.

Because the protein is also located on the outer membrane of the vesicles, they could also be used to induce an immune response. Thus, for example, flu epitopes may be loaded into the vector and expressed on the outside of the vesicles to induce immune response to flu virus.

Example 4

Effect of the Secretion Antagonist (HIV NEF SMRWT Peptide) on HIV-1 GAGWT-GFP-Induced Secretion Cells were co-transfected with 0.5 µg of pQBI-HIV Gag-GFP (expresses wild type Gag protein) and either 0.5 µg of HIV-1 Nef SMRwt, SMRmut peptide, sM1 peptide or untransfected controls with Chariot for 48 hours. The conditioned supernatants from these cultures were assayed for GFP fluorescence by plate reader. The results are shown in Table II. Particle secretion levels are displayed relative to the untransfected control which is arbitrarily set as 1× (negative control; 100%).

TABLE II

Increase in Secretion (relative to untransfected cells) Fluorescent Plate Reader Assay

| Cell Lines | HIV-1 Gag-GFP/SMRwt | HIV-1 Gag-GFP/SMRmt | GFP/sM1 | Untransfected |
|---|---|---|---|---|
| Jurkat | 47.46x 1y | 58.22x 1.22y | 1.09x | 1x |
| HEK293 | 24.22x 1y | 25.96x 1.08y | 2.05x | 1x |
| THP-1 | 41.3x 1y | 45.06x 1.08y | 0.85x | 1x |
| U937 | 43.95x 1y | 43.82x 1y | 1.05x | 1x |
| Cell Lines | HIV-1 Nef-GFP/SMRwt | HIV-1 Nef-GFP/SMRmt | GFP/sM1 | Untransfected |
| H | 2.3x 1.0y | 57.04x 24.8y | 1.05x | 1x | x—exp condition/UT;
y—SMRmt/SMRwt

Gag has been shown to be secreted from Gag-transfected cells in what are called 'virus-like particles'. These virus-like particles are very much like vesicles. It has been suggested that the virus (which has been described as a Gag type vesicle) is released from cells via the exosome pathway. The secretion antagonist SMRwt had no effect on Gag virus-like particle release. This suggests that the Gag trafficking pathway and the Nef trafficking pathway differ at least one point. This point is that factor(s) in the pathway that the antagonist manipulates.

Example 5

Effect of the Secretion Antagonist (HIV NEF SMRWT Peptide) ON HIV-1 GAGWT-GFP-Induced Secretion in Presence of WTNEF Protein Cells were transfected with the pQBI-HIV Gag-GFP construct, wtNef-RFP, and either the antagonist (SMRwt peptide), the negative control SMRmt peptide, or a random peptide sM1 with Chariot for 48 hours. The conditioned supernatants from these cultures were assayed for GFP fluorescence by plate reader. The results are shown in Table III. Particle secretion levels are displayed relative to the untransfected control which is arbitrarily set as 1× (negative control; 100%).

TABLE III

Inhibition of Secretion (relative to untransfected cells) Fluorescent Plate Reader Assay

| Cell Lines | Gag-GFP + HIV-1wtNef-RFP + SMRwt | Gag-GFP + HIV-1wtNef-RFP + SMRmt | Gag-GFP + HIV-1wtNef-RFP + sM1 | Untransfected |
|---|---|---|---|---|
| Jurkat | 1.3x | 55.73x | 61.99x | 1x |
|  | 1.16x | 43.51x | 40.36x | 1x |
| THP-1 | 0.95x | 49.27x | 43.11x | 1x |
| Monocyte | 0.91x | 22.24x | 20.51x | 1x |

As shown in Table III, in the presence of wtNef-RFP the SMRwt antagonist peptide blocks release of Gag virus-like particles. These results show that the SMRwt does not antagonize Gag VLP formation and release when Gag is in the cell alone, but SMRwt does antagonize Gag VLP formation and release when Gag and Nef are both in a cell. It suggests that Nef is directing Gag release into a pathway different from the pathway Gag takes when it is in a cell by itself. It also explains why the SMRwt peptide can block HIV virus release but not Gag virus-like particle release (when only Gag is present).

As shown in Table III, In the presence of wtNef-RFP the SMRwt antagonist peptide does block the release of Gag virus-like particles in the presence of wtNef-RFP.

Example 6

Cellular Toxicity Assay for SMRWT Peptide

SMRwt or SMRmut (negative control) peptide alone were transfected into Jurkat cells using Chariot. The transfected cells were allowed to grow for 48 hours. The cells were assayed by Fluorescein diacetate (FD; taken up by live cells and converted to FITC making cells fluoresce green) and propidium iodide (PI; diffuse across porous membranes of dying cells fluoresing red inside those cells) for cytotoxicity.

Figure 12:
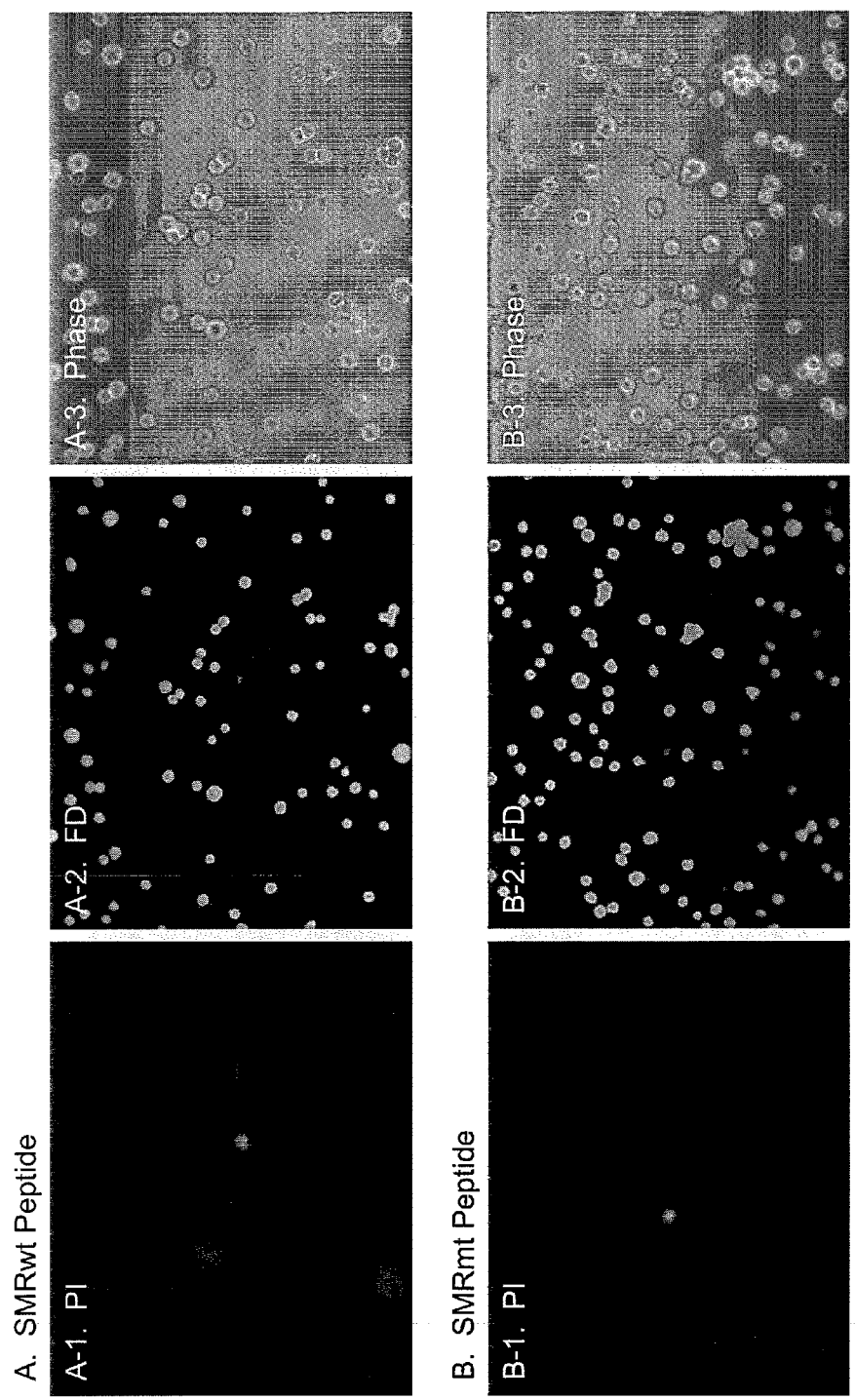
FIG. 12 is a composite of pictures showing the result of cellular toxicity assay for cells transfected with SMRwt or SMRmt peptide. Panels A-1 and B-1: Propidium iodide staining of cells transfected with SMRwt and SMRmt peptide, respectively. Panels A-2 and B-2: Fluorescein diacetate staining of cells transfected with SMRwt and SMRmt peptide, respectively. Panels A-3 and B-3: Phase microscope image of cells transfected with SMRwt and SMRmt peptide, respectively.

As shown in FIG. 12, only a very small number of dying cells (<2%) were detected in SMRwt transfected cells (panel A-1). Further, the number of dying cells in SMRwt transfected cells is similar to that seen in SMRmut transfected cells (Panel B-1). These results suggest that the SMRwt antagonist has very little or no cytotoxicity in Jurkat cells.

Example 7

Identifying Cellular Factors that Interact with the Antagonist

A: Identification of Cellular Factors that Bind the SMRwt Peptide and Regulate Secretion.

SMRwt vs. SMRmt peptides were used in conjunction with FLAG immuno-precipitation on Jurkat cell lysates to pulldown cellular factors that interacted with the SMRwt antagonist, but not with the SMRmt negative control. The cellular factor(s) that interact with the antagonist are analyzed by the FLAG IP assay. Briefly, cell lysates are combined with AminoLink Plus resin coupled to FLAG-tagged SMR peptides. SMR-specific cellular proteins (ROY) bind to the SMR peptides on the resin. Non-specific contaminants (G BIV) are washed off of the resin and removed by centrifugation. The SMR-specific cell proteins (ROY) are eluted and collected. Some strongly bound contaminants (V) are also eluted and collected.

Figure 13:
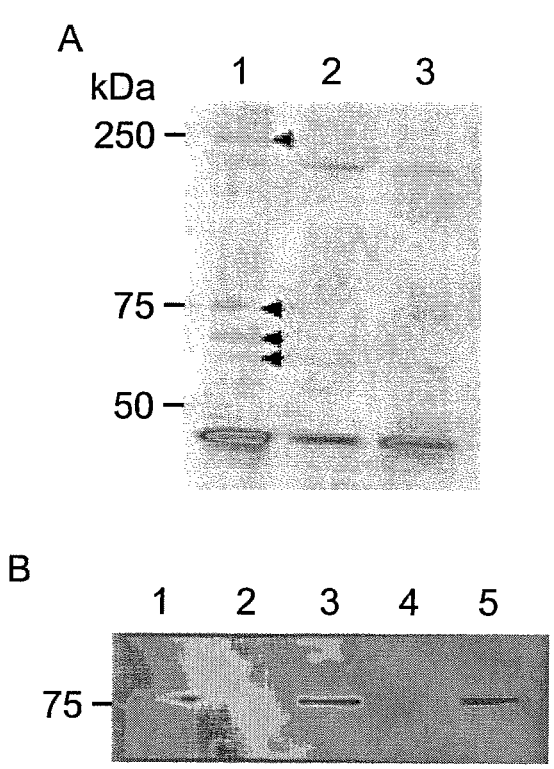
FIG. 13 is a composite of pictures showing immunoprecipitation with SMRwt or SMRmt peptide (panel A) and identification of the 75 kD SMR-specific protein by Western blot.

The pulldown products were separated on SDS PAGE ((FIG. 13, panel A). Bands that appeared in the SMRwt lane but not in the SMRmt lane were cut out and purified. Five bands were identified and purified in this manner (FIG. 13, panel A). MALDI TOF MS/MS and LC/MS/MS were used to identify these protein products and were found to be Mortalin/GRP75; Myosin 10; Vimentin; GRP78; HSC70. Among these proteins, mortalin/GRP75 is a member of the Hsp70 family of chaperones. It is located in both mitochondria and cytoplasm, and has been implicated in multiple functions ranging from stress response, intracellular trafficking, antigen processing, and control of cell proliferation, differentiation, and tumorigenesis. Mortalin interacts with p53, and is shown to be involved in apoptosis and vesicle transport (MAC complex). It is also found in microvesicles released by tumor cells.

The gel was also Western probed with α-Mortalin antibody. A protein with a molecular weight of ~75 kDa was detected in the lanes containing the cell lysate, the antagonist eluate, and the antagonist affinity resin (FIG. 13, panel B, Lanes 1, 3, and 5), but not in the negative control or negative control peptide eluate's lanes (FIG. 13, panel B, Lanes 2 and 4).

Mortalin Antibody Inhibition of Vesicle Secretion

Figure 14:
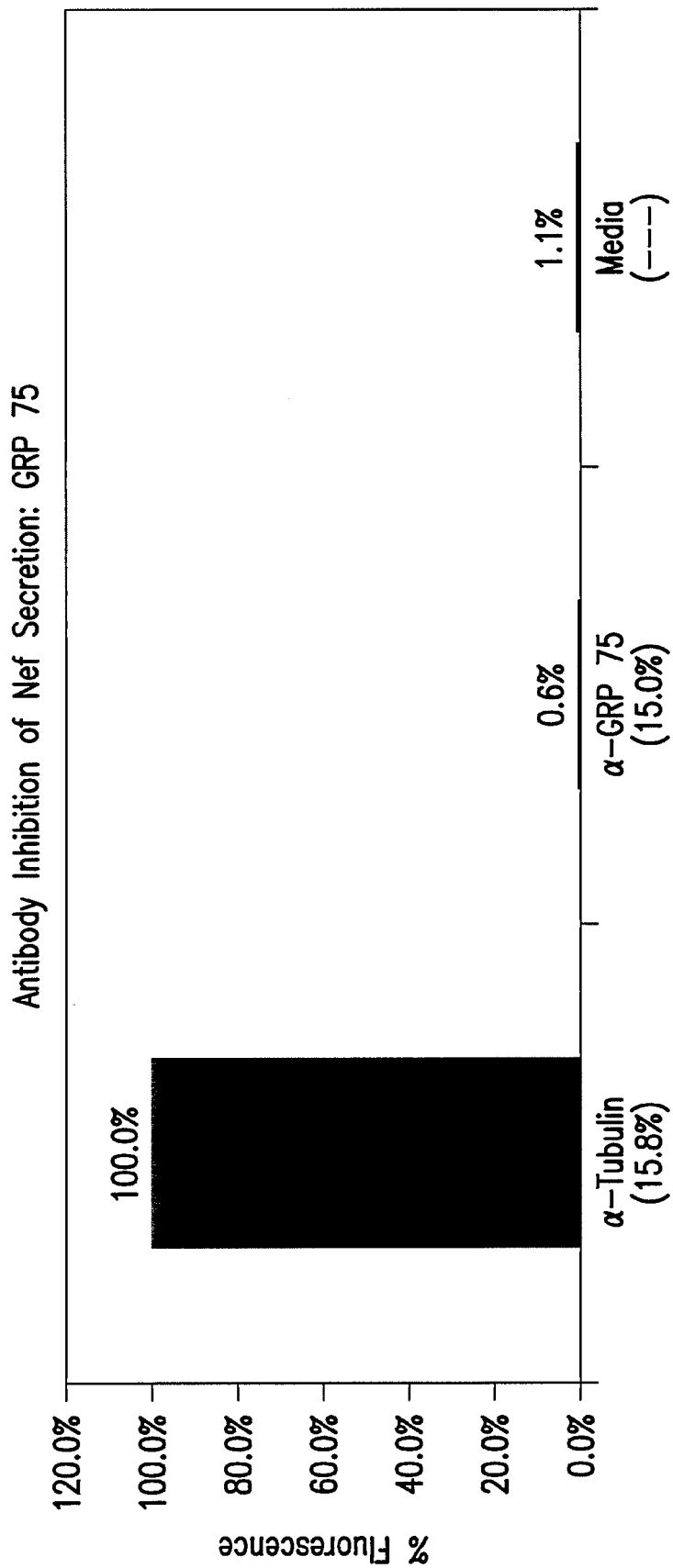
FIG. 14 is a diagram showing Mortalin antibody inhibition of Nef secretion.

Chariot transfection of a Mortalin/GRP75 antibody into Jurkat cells with the wtNefGFP control was used to knockdown the endogenous Mortalin/GRP75 protein to observe the effect on Nef-induced secretion (FIG. 14). A-tubulin antibody was chariot transfected into matched cells as a negative control. We observed that the Mortalin/GFP75 antibody blocked NEf-induced secretion while the a-tubulin antibody had no effect on Nef-induced secretion. This showed that Mortalin is important in Nef-induced exosome secretion. Mortalin antibody hybridizes to eluate band.

Mortalin is also known as glucose-regulated protein 75 (GRP75), or peptide-binding protein 74 (PBP74). Mortalin is a 679 amino acid long, uninducible member of the heat shock protein 70 families. It has a high degree of identity with other family members including Escherichia coli DnaK. Although the crystal structure of Mortalin has not been deduced, based on the evolutionary conservation within the Hsp70 family, it is expected to have two principal domains, the N-terminal ATPase nucleotide binding domain (NBD) and C-terminal substrate binding domain (SBD), joined by a protease-sensitive site. The NBD is highly conserved across the family, while the SBD displays significant diversity possibly explaining the variation among Hsp70 family members in substrate specificity. Its chaperone activities are intimately linked with the ATP-hydrolysis function.

Mortalin has been found to be localized to the mitochondria as well as to various cytoplasmic vesicles, including early endocytic vesicles (See, e.g., Kanai et al., Genes Cells, 2007, 12:797-810; Kaul et al., Exp. Gerontol., 2002, 37:1157-1164; Singh et al., Exp Cell Res, 1997, 234:205-216 and Van Buskirk et al., J. Immunol. 1991, 146:500-506). Mortalin binds directly to several proteins (e.g., p53 and FGF-1) and regulates their intracellular trafficking (see, e.g., Kaul et al., J Biol Chem, 2005, 280:39373-39379; Mizukoshi et al., Biochem Biophys Res Commun, 2001, 280:1203-1209; Mizukoshi et al., Biochem J, 1999, 343:461-466; and Prudovsky et al., J Cell Biochem, 2008, 103:1327-1343) through the non-classical pathway (i.e., exosomal pathway). Cells under attack by the host immune system release membrane vesicles through Mortalin expression, and Mortalin is found in those vesicles (Pilzer et al., Int Immunol, 2005, 17:1239-1248). Mortalin is also found in the exosomes released by various tumor cells (Choi et al., J Proteome Res, 2007, 6:4646-4655; Staubach et al., Proteomics, 2009).

Mortalin has been found to play multiple major functions in the cell (reviewed in Kaul et al., Exp Ger ontol, 2007, 42:263-274). It serves a major housekeeping function in the cellular translocation system of import and export of proteins. Although not induced by heat, mild stress responses induce Mortalin allowing it to serve as a guardian against stress and apoptosis. Decreased expression of Mortalin, or expression of mutant forms of Mortalin, lead to senescence, while increased expression of Mortalin leads to immortality, with the aberrant form being cancer.

Evidence clearly implicates Mortalin in transformation of normal cells to cancer cells, as well as in the chemotherapy resistance of those cells. Mortalin was found to be overexpressed in tumor cells of various origins (Wadhwa et al., Int J Cancer, 2006, 118:2973-2980). The murine Mortalin was found to change its subcellular location from mitochondria, in normal cells, to the cytosol in cancerous cells (Wadhwa et al., J Biol Chen 1998, 273:29586-29591). Mortalin was found to interact with p53. Further, this interaction promotes sequestration of p53 in the cytoplasm, thereby inhibiting its nuclear activity (Kaul et al., Supra 2007, 42:263-274; Yi et al., Mol Cell Proteomics, 2008, 7:315-325; Czamecka et al., Cancer Biol Ther, 2006, 5:714-720), inducing the resistance of some tumors to radiotherapy and chemotherapy. Finally, as discussed above, Mortalin has been linked with intracellular trafficking leading to exosome release and has been shown to be in exosomal vesicles (Pilzer et al. pringer Semin Immunopathol, 2005, 27:375-387; Choi et al., J Proteome Res, 2007, 6:4646-4655; Staubach et al., Proteomics, 2009). Tumor cells (e.g., breast tumors) have been found to secrete, in a regulated manner, exosomes that carry tumor antigens, and are capable of presenting these antigens or transmitting them to antigen presenting cells (Yu et al., J Immunol, 2007, 178:6867-6875). These tumor exosomes cause immune suppression through immune cell killing or dysregulation, thereby promoting a state of immune privilege that allows for tumor growth. Thus, through a variety of mechanisms, the tumor manipulates Mortalin enhancing its own fitness.

Heat shock 70 family proteins have been found to be linked with breast cancer. They have clear associations with poor differentiation, lymph node metastasis, increased cell proliferation, block of apoptosis, and higher clinical stage in breast cancer. All these morphologies are markers of poor clinical outcome (Calderwood et al., Int J Hyperthermia, 2008, 24:31-39; Calderwood et al., Trends Biochem Sci, 2006, 31:164-172; Ciocca et al., Cell Stress Chaperones, 2005, 10:86-103). Additionally, it has been clearly shown that over-expression of Mortalin contributes to carcinogenesis in many cell types, specifically having been observed in breast cancer cells (Wadhwa et al., Int J Cancer, 2006, 118:2973-2980).

It is clear from the literature that Mortalin is a potential target for cancer immunotherapy, and there are a number of studies looking to develop therapeutics (Wadhwa et al., Cancer Therapy, 2010, 1:173-178; Walker et al., Am J Pathol, 2006, 168:1526-1530; Deocaris et al., Cancer Lett, 2007, 252:259-269; Pilzer et al., Int J Cancer, 2009; Parolini et al., J Biol Chem, 2009). For example, MKT-077 is a mitochondrion-seeking delocalized cationic dye that causes selective death of cancer cells (Deocaris et al., Cancer Lett, 2007, 252:259-269). Its cellular targets include oncogenic Ras, F-actin, telomerase, and Mortalin (hmot-2)/mthsp70 (Parolini et al., J Biol Chem, 2009). MKT-077 binds to the nucleotide-binding domain (NBD) of Mortalin and causes tertiary structural changes in the protein, inactivating its chaperone function, and inducing senescence in human tumor cell lines. In clinical trials, this molecule was found to cause renal toxicity, although there is some evidence now suggesting lower doses could be less toxic.

Example 8

Other Drugs that Inhibit Vesicle/Virus Release

The HIV Nef SMRwt peptide may be used in conjunction with drugs that have been approved by the FDA for use in other conditions and have been identified as having efficacy in blocking virus release as well as vesicle release. Examples of such drags are: dimethyl amiloride and omeprazole.

Figure 15:
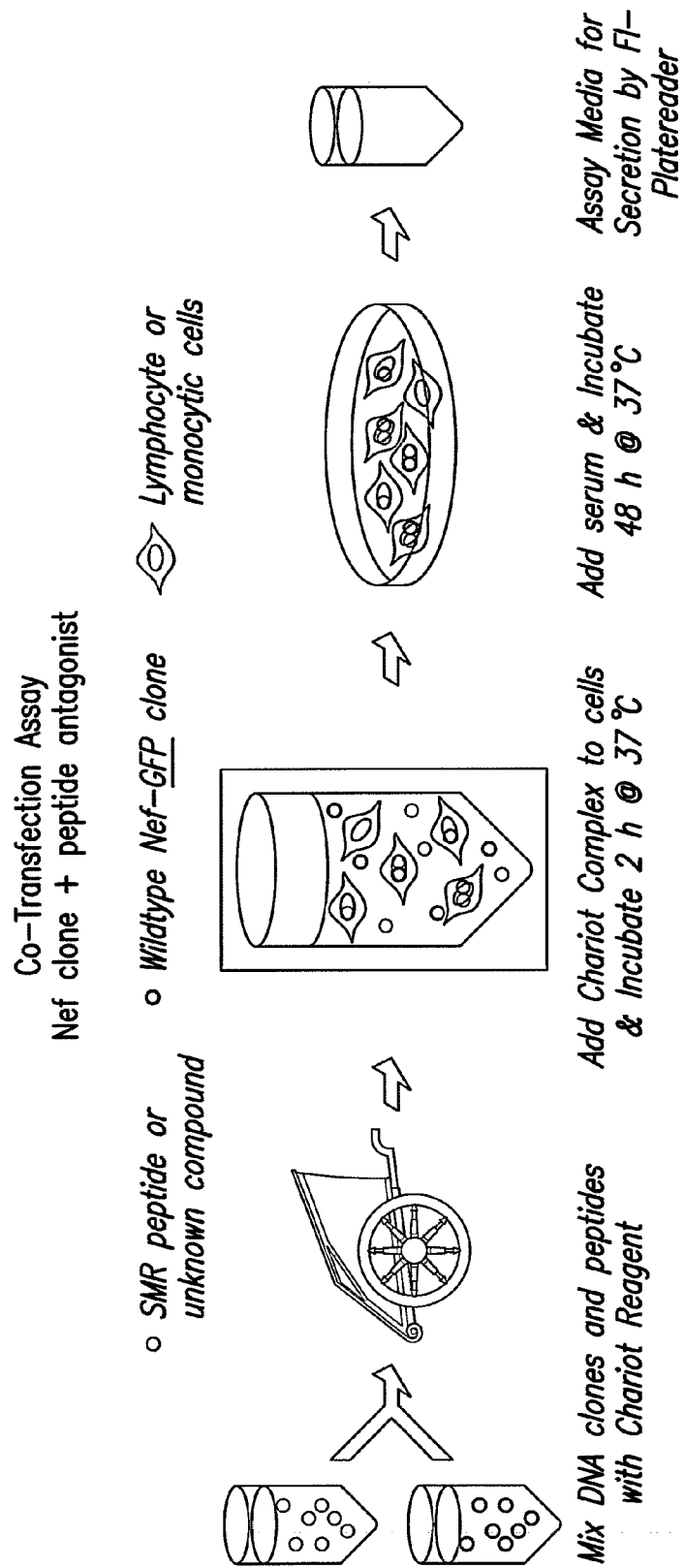
FIG. 15 is a diagram showing a cotransfection assay for monitoring effect of SMR peptide or unknown compound on Nef secretion.
Figure 16:
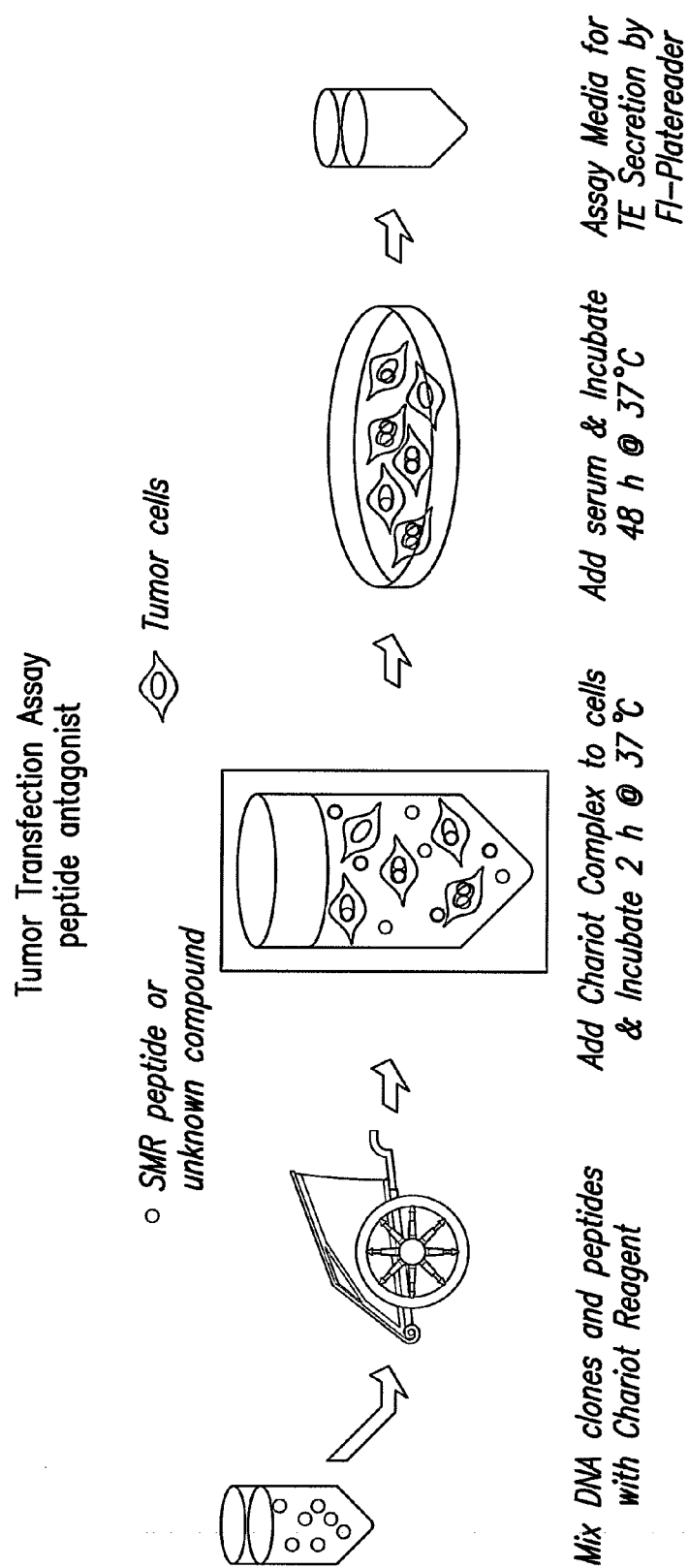
FIG. 16 is a diagram showing a cotransfection assay for monitoring the effect of SMR peptide or unknown compound on tumor vesicle secretion.

A cotransfection assay has been developed that can be used to screen for agents that block secretion. In procedure one (FIG. 15), NefGFP, NefRFP, or Nef linked to any fluorescent tag, is transfected into a cell line and the cell is treated with an agent or chemical during a 48 hr incubation period. Then, at 48 hr post transfection, the conditioned supernatant is assayed for the fluorescent molecule (by various techniques). In procedure two (FIG. 16), the cell is treated with a fluorescent label like N—Rh-PE that will label endogenously made exosomes. The cell is allowed to incubate for at least 24 hours in the presence or absence of a chemical or small peptide antagonist. The conditioned supernatant is then assayed for N—Rh-PE labeled microvesicles/exosomes (by various techniques). The lack of the fluorescent tag in the conditioned supernatant is a sign that the chemical agent has blocked the exosome secretion pathway blocking Nef induction of that pathway. This procedure should be able to be modified to develop a high throughput assay for screening of agents that block secretion.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present embodiment, which is defined by the following claims. The claims are intended to cover the claimed components and steps in any sequence which is effective to meet the objectives there intended, unless the context specifically indicates the contrary.

What is claimed is:

1. A method for reducing the formation of virion particles in an HIV-infected cell, comprising:
    contacting an HIV-infected cell in a human subject with a peptide containing at least two SEQ ID NO: 1 motifs and having a length of 10-100 amino acids in an amount effective to reduce virion formation in said cell.

2. The method of claim 1, wherein said peptide comprises at least one SEQ ID NO: 1 motif at the N-terminal end of the peptide.

3. The method of claim 1, wherein said peptide comprises at least one SEQ ID NO: 1 motif at the C-terminal end of the peptide.

4. The method of claim 1, wherein said peptide comprises the amino acid sequence of SEQ ID NO: 2.

5. The method of claim 1, wherein said peptide comprises the amino acid sequence of SEQ ID NO: 3.

6. A method for reducing the formation of virion particles in an HIV-infected cell, comprising:
    contacting an HIV-infected cell in a human subject with a polynucleotide encoding a peptide containing at least two SEQ ID NO: 1 motifs and having a length of 10-100 amino acids in an amount effective to reduce virion formation in said cell, wherein said polynucleotide is capable of expressing said peptide in said cell.

7. The method of claim 6, wherein said peptide comprises the amino acid sequence SEQ ID NO: 2.

8. The method of claim 6, wherein said peptide comprises the amino acid sequence of SEQ ID NO: 3.

9. The method of claim 6, wherein said peptide comprises at least one SEQ ID NO: 1 motif at the N-terminal end of the peptide.

10. The method of claim 6, wherein said peptide comprises at least one SEQ ID NO: 1 motif at the C-terminal end of the peptide.

11. A method for reducing the formation of virion particles in an HIV-infected cell, comprising:
    contacting an HIV-infected cell in a human subject with an expression vector comprising a polynucleotide encoding a peptide containing at least two SEQ ID NO: 1 motifs and having a length of 10-100 amino acids in an amount effective to reduce virion formation in said cell, wherein said expression vector is capable of expressing said peptide in said cell.

12. The method of claim 11, wherein said peptide comprises the amino acid sequence SEQ ID NO: 2.

13. The method of claim 11, wherein said peptide comprises the amino acid sequence of SEQ ID NO: 3.

14. The method of claim 11, wherein said peptide comprises at least one SEQ ID NO: 1 motif at the N-terminal end of the peptide.

15. The method of claim 11, wherein said peptide comprises at least one SEQ ID NO: 1 motif at the C-terminal end of the peptide.

16. The method of claim 11, wherein said expression vector is a viral vector.

17. The method of claim 11, wherein said expression vector is a non-viral vector.

* * * * *